US012636506B2

(12) United States Patent
Villamil et al.

(10) Patent No.: US 12,636,506 B2
(45) Date of Patent: May 26, 2026

(54) STRAIN-RELIEF/LEAD ASSEMBLY ELECTRICALLY AND MECHANICALLY CONNECTED TO AN ACTIVE MEDICAL DEVICE

(71) Applicant: GREATBATCH LTD., Clarence, NY (US)

(72) Inventors: Luis Daniel Villamil, Montevideo (UY); Ignacio Agustin Armesto, Montevideo (UY); Hugh D. Hestad, Edina, MN (US)

(73) Assignee: Greatbatch Ltd., Clarence, NY (US)

( * ) Notice: Subject to any disclaimer, the term of this patent is extended or adjusted under 35 U.S.C. 154(b) by 326 days.

(21) Appl. No.: 18/199,702

(22) Filed: May 19, 2023

(65) Prior Publication Data

US 2023/0372721 A1     Nov. 23, 2023

Related U.S. Application Data

(63) Continuation of application No. 18/199,162, filed on May 18, 2023.

(60) Provisional application No. 63/344,087, filed on May 20, 2022.

(51) Int. Cl.
| | |
|---|---|
| *A61N 1/375* | (2006.01) |
| *A61B 5/00* | (2006.01) |
| *A61B 5/25* | (2021.01) |
| *A61N 1/05* | (2006.01) |
| *A61N 1/08* | (2006.01) |
| *A61N 1/378* | (2006.01) |

(52) U.S. Cl.
CPC .............. *A61N 1/3754* (2013.01); *A61B 5/25* (2021.01); *A61B 5/4836* (2013.01); *A61B 5/686* (2013.01); *A61N 1/05* (2013.01); *A61N 1/0563* (2013.01); *A61N 1/08* (2013.01); *A61B 2562/227* (2013.01); *A61N 1/37512* (2017.08); *A61N 1/378* (2013.01)

(58) Field of Classification Search
CPC .................................................. A61N 1/3754
See application file for complete search history.

(56) References Cited

U.S. PATENT DOCUMENTS

| | | | | |
|---|---|---|---|---|
| 4,245,642 | A * | 1/1981 | Skubitz | ................ A61N 1/3752 607/37 |
| 7,794,256 | B1 | 9/2010 | Sochor | |
| 8,162,684 | B1 * | 4/2012 | Sochor | ................ A61N 1/3754 439/289 |
| 9,011,169 | B2 | 4/2015 | Russell et al. | |
| 2004/0106964 | A1 | 6/2004 | Fischer et al. | |

* cited by examiner

*Primary Examiner* — William J Levicky
(74) *Attorney, Agent, or Firm* — Michael P. Scalise

(57) ABSTRACT

An active medical device has a feedthrough with at least two terminal pins that are connected to electronic components in the device housing. A lead connector is connected to a strain-relief device for a lead. The lead connector supports at least two proximally-facing C-shaped inserts with an annular spring nested therein that are detachably connected to the device terminal pins to thereby connect the device electronic components to the lead electrodes. The device housing has a length extending along a longitudinal axis, and secondary axes of the terminal pins connected to the C-shaped inserts/annular springs are aligned parallel to the axis with imaginary extensions of the connector axes extending into the device housing.

13 Claims, 18 Drawing Sheets

STRAIN-RELIEF/LEAD ASSEMBLY ELECTRICALLY AND MECHANICALLY CONNECTED TO AN ACTIVE MEDICAL DEVICE

CROSS-REFERENCE TO RELATED APPLICATIONS

This application is a continuation of U.S. application Ser. No. 18/199,162, filed on May 18, 2023, which claims priority to U.S. Provisional Application Ser. No. 63/344,087, filed on May 20, 2022.

BACKGROUND OF THE INVENTION

1. Field of the Invention

The present invention relates to the field of implantable medical devices. More particularly, the present invention relates to a miniature-sized active medical device (AMD) that is designed to deliver electrical stimulation to a patient or sense biological signals from body tissue. A miniature-sized AMD is defined as a medical device that has a volume of less than about 3 cc. The AMD can be implanted in a patient's body or worn externally on the body.

The desire to make AMDs as small as possible is an active area of innovation. Implanting a miniature-sized AMD is advantageous over implanting a conventionally-sized pulse generator for many reasons. Chief among them is that the implantation procedure can be performed with far less surgical trauma to the patient. As long as the miniature AMD has the same or similar functionality as an AMD of a conventional size, subjecting the patient to less trauma represents an advancement in the industry. This includes implanting a miniature-sized neurostimulator for pain therapy. Additionally, a miniature-sized neurostimulator can be applied to many more nerves, particularly to smaller nerves, than a relatively larger conventionally-sized AMD. Further, an externally worm miniature AMD would be expected to be less bothersome to a patient than a larger version of the same device.

2. Prior Art

A conventional active medical device has a header assembly that is detachably connected to a lead provided with at least two spaced-apart electrodes. The electrodes, which are configured to send electrical pulses to the surrounding body tissue or sense biological signals from the tissue, are assembled into the distal end of the lead to contact the surrounding tissue while the proximal lead end is received in the header assembly of the medical device. The device header has a number of terminal contacts or terminal blocks that are configured to electrically connect to the lead. Typical configurations have a plurality of terminal contacts aligned in-line or as a co-axial system with insulation positioned between adjacent contacts. However, there are size limitations in how small the industry can miniaturize such in-line lead attachment configurations using current design technology.

Other efforts to miniaturize AMDs are focused on integrating the active medical device with the lead into a single device. Although this simplifies the connection between the medical device and its pacing/sensing lead, such medical devices cannot be customized according to the physical characteristics of the implantation procedure or the patient's medical condition.

Therefore, there is an ongoing need for an AMD, whether implantable or intended to be worn externally, that is detachably connectable to a lead to provide both stimulation and sensing capability where the header assembly has a high density of electrical contacts for connecting a stimulation/sensing lead to the medical device, but in a device having a volume that is less than about 3 cc. A smaller medical device is easier to implant in a patient and would be expected to cause less trauma to the patient. A smaller medical device is also expected to be less bothersome to a patient.

SUMMARY OF THE INVENTION

The present miniaturized AMD has a header assembly that provides a lead contact system where the plurality of terminal contacts are not aligned in a co-axial array. This enables the AMD to have a higher density of terminal contacts for connecting a stimulation/sensing lead to the medical device than in a conventional device header. Since the terminal contact array is not aligned in the axial direction of the lead body, the device/lead assembly of the present invention has a relatively smaller volume. Also, the lead is desirably small enough to pass through a catheter or sheath into a desired implantation site prior to being connected to the medical device. This provides the physician with greater flexibility in selecting the proper lead length and electrode pattern. In that respect, the present miniaturized AMD enables a physician to match the medical device with a desired lead length and electrode pattern prior to implanting the lead and the AMD.

Thus, the purpose of the present inventive subject matter is to reduce the size of an AMD by reducing the volume of the connection between the medical device and its associated lead. Size reduction is realized by reconfiguring the connections between the electrical contacts at the proximal end of the lead and the terminal contacts connected to terminal pins of the feedthrough for the medical device so that the terminal contacts are not in an in-line configuration, as is customary. Instead, the device housing has a length extending along a longitudinal axis, and secondary axes of the terminal pins connected to the connector pins in turn connected to the lead are aligned parallel to the longitudinal axis. In addition to reducing the volume of the lead-to-medical device connection, this connection structure reduces the number of process steps needed to insulate the terminal contacts from each other and from other parts of the medical device. The total volume of the connection between the AMD and its associated lead is also reduced.

In that respect, the present invention is directed to a medical device that comprises a device housing containing an electrical power source connected to a printed circuit board supporting at least one electronic component. A feedthrough is welded into an opening in the device housing. The feedthrough comprises a ferrule defining a ferrule opening extending to a ferrule device side end surface and a ferrule body fluid side end surface. An insulator is hermetically sealed to the ferrule in the ferrule opening and extends to an insulator device side residing at or adjacent to the ferrule device side end surface and an insulator body fluid side residing at or adjacent to the ferrule body fluid side end surface. At least a first via and a second via extend through the insulator to the insulator device and body fluid sides. A first terminal pin and a second terminal pin are hermetically sealed to the insulator in the respective first and second vias. The first and second terminal pins each have a device side portion extending outwardly beyond the device side of the insulator to connection to the electronic component, and a body fluid side portion extending outwardly beyond the body fluid side of the insulator for electrical connection to a lead. The device housing also has a pair of first and second spaced-apart arms that extend distally from the body fluid side surface of the ferrule. The first and second arms are provided with respective first and second inwardly-facing detents.

The present invention also has a strain-relief device that is fixedly connected between a lead connector and a lead having at least two electrodes. The lead connector comprises an annular connector sidewall extending from a connector device side end surface to a connector body fluid side end surface. A lateral web residing between the connector device side and body fluid side end surfaces is provided with at least a first and a second connector openings. A first connector pin resides in the first connector opening and a second connector pin resides in the second connector openings. The first and second connector pins each have a device side portion extending outwardly beyond a device side of the connector web and a body fluid side portion extending outwardly beyond a body fluid side of the connector web. There are also first and second lateral recesses provided in the annular connector sidewall.

That way, with the first and second detents of the first and second spaced-apart extending arms of the feedthrough received in the first and second lateral recess of the lead connector, the medical device is connected to the strain-relief device. This electrically connects the device side portions of the first and second feedthrough terminal pins to the at least one electronic component contained in the device housing. The body fluid side portions of the first and second terminal pins are electrically connected to the device side portions of the first and second connector pins with the terminal pins connected to the connector pins being aligned along a plurality of secondary axes that are parallel to a longitudinal axis of the device housing. The body fluid side portions of the connector pins are electrically connected to the first and second electrodes of the lead.

These and other aspects of the present invention will become increasingly more apparent to those skilled in the art by reference to the following detailed description and to the appended drawings.

DETAILED DESCRIPTION OF THE PREFERRED EMBODIMENTS

As used herein, the term "active medical device" means a medical device, whether implantable or worn externally, that is designed to deliver electrical stimulation to a patient or sense biological signals from body tissue, or both stimulate and sense.

Figure 1:
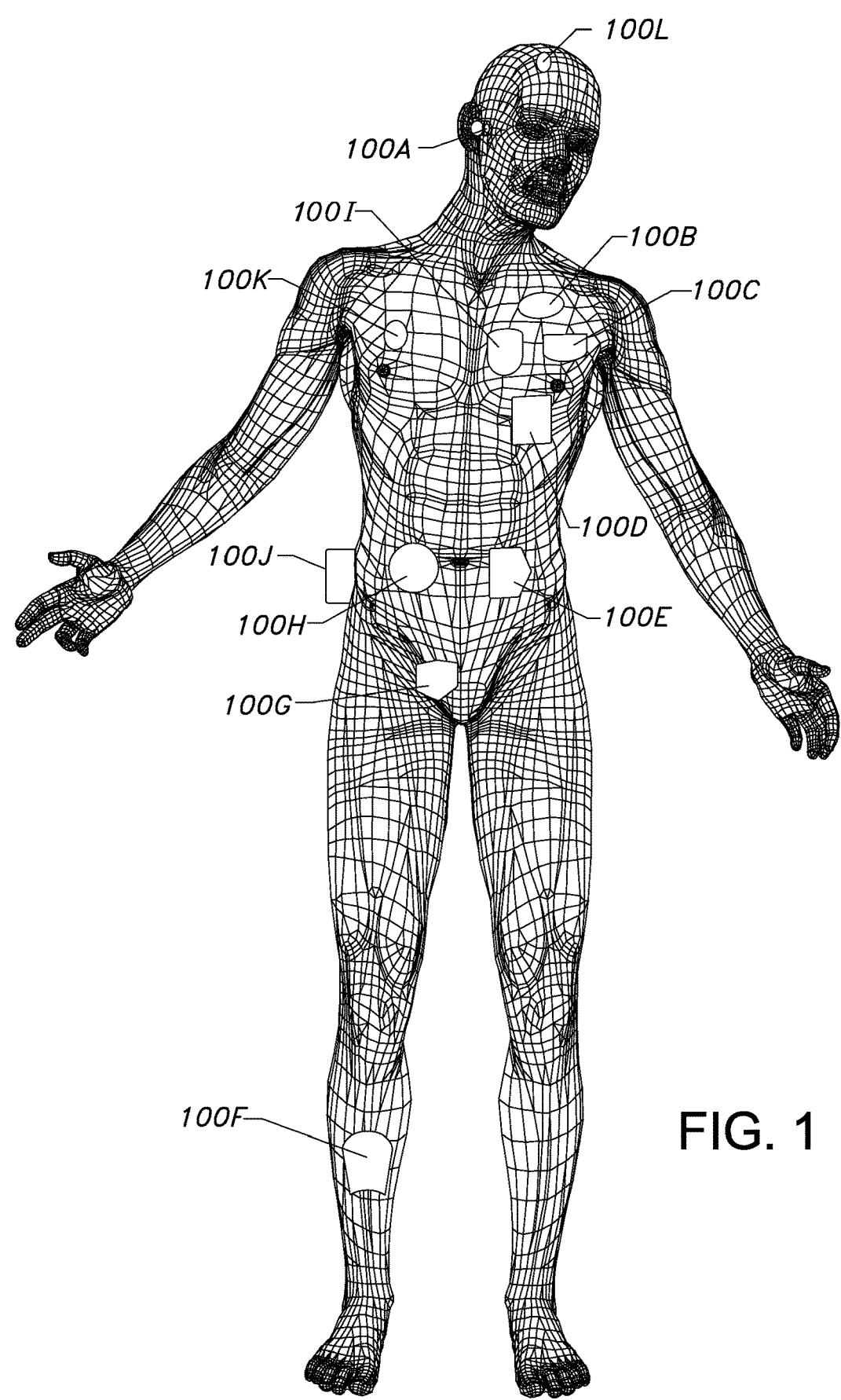
FIG. 1 is a wire formed diagram of a generic human body showing a number of medical devices 100A to 100L according to the present invention that can either be implanted in a patient's body tissue or attached externally to the body.

Turning now to the drawings, FIG. 1 is a wire form diagram of a generic human body illustrating various types of active implantable and external medical devices according to the present invention that can either be implanted in a patient's body or attached externally to the body.

Numerical designation 100A represents a family of hearing devices which can include the group of cochlear implants, piezoelectric sound bridge transducers, and the like.

Numerical designation 100B represents a variety of neurostimulators, brain stimulators, and sensors. Neurostimulators are used to stimulate the Vagus nerve, for example, to treat epilepsy, obesity, and depression. Brain stimulators are pacemaker-like devices and include electrodes implanted deep into the brain for sensing the onset of a seizure and also providing electrical stimulation to brain tissue to prevent a seizure from actually occurring. The lead wires associated with a deep brain stimulator are often placed using real time MRI imaging. Sensors include optical sensors, motion sensors, acoustic sensors, pressure sensors, analyte sensors, and electromagnetic sensors, among others.

Numerical designation 100C shows a cardiac pacemaker which is well-known in the art.

Numerical designation 100D includes the family of left ventricular assist devices (LVADs), and artificial heart devices.

Numerical designation 100E includes a family of drug pumps which can be used for dispensing insulin, chemotherapy drugs, pain medications, and the like.

Numerical designation 100F includes a variety of bone growth stimulators for rapid healing of fractures.

Numerical designation 100G includes urinary incontinence devices.

Numerical designation 100H includes the family of pain relief spinal cord stimulators and anti-tremor stimulators.

Numerical designation 100H also includes an entire family of other types of neurostimulators used to block pain.

Numerical designation 100I includes a family of implantable cardioverter defibrillator (ICD) devices and also the family of congestive heart failure devices (CHF). This is also known in the art as cardio resynchronization therapy devices, otherwise known as CRT devices.

Numerical designation 100J illustrates an externally worn pack. This pack could be an external insulin pump, an external drug pump, an external neurostimulator or even a ventricular assist device.

Numerical designation 100K illustrates one of various types of EKG/ECG external skin electrodes which can be placed at various locations on the patient's body.

Numerical designation 100L represents external EEG electrodes that are placed on the patient's head.

Figure 2:
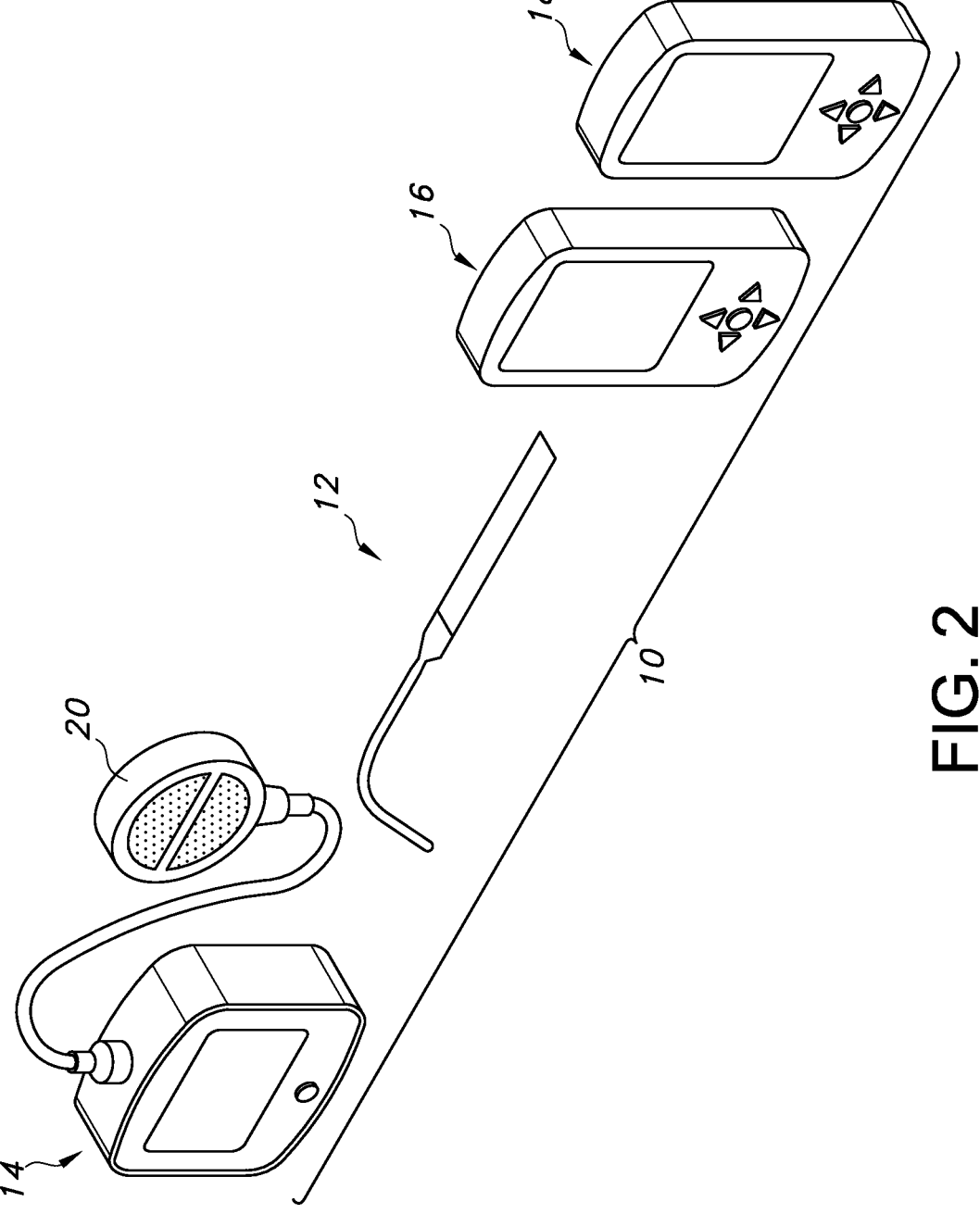
FIG. 2 is a simplified block diagram of an exemplary medical device system 10 according to the present invention.

To provide context to the various medical devices 100A to 100L illustrated in FIG. 1, FIG. 2 illustrates a simplified block diagram of an exemplary medical device system 10 according to the present invention. The medical device system 10 includes an active medical device (AMD) 12, which is any one of various types of the medical devices that include a lead, whether implantable or external, as described above with reference to FIG. 1. The medical device system 10 also has an external charger 14, a patient programmer 16, and a clinician programmer 18.

The patient programmer 16 and the clinician programmer 18 may be portable handheld devices, such as a smartphone or other custom device, that are used to configure the AMD 12 so that the AMD can operate in a desired manner. The patient programmer 16 is used by the patient in whom the AMD 12 is implanted. The patient may adjust the parameters of electrical stimulation delivered by the AMD 12, such as by selecting a stimulation program, changing the amplitude and frequency of the electrical stimulation, among other parameters, and by turning stimulation on and off. Additionally, the patient programmer 16 may collect and display data being collected by the device 12 and alert the patient to potential health risks.

The clinician programmer 18 is used by medical personnel to configure the other system components and to adjust stimulation parameters that the patient is not permitted to control. These include setting up stimulation programs among which the patient may choose and setting upper and lower limits for the patient's adjustments of amplitude, frequency, and other parameters. It is also understood that although FIG. 2 illustrates the patient programmer 16 and the clinician programmer 18 as two separate devices, they may be integrated into a single programmer in some embodiments.

Electrical power can be delivered to the AMD 12 through an external charging pad 20 that is connected to the external charger 14. In some embodiments, the external charging pad 20 is configured to directly power the AMD 12 or it is configured to charge a rechargeable electrical power source (not shown) of the AMD. The external charging pad 20 can be a hand-held device that is connected to the external charger 14, or it can be an internal component of the external charger. The external charger 14 and the charging pad 20 can also be integrated into a single device that is strapped on or attached to the patient with adhesive, and the like.

Figure 3:
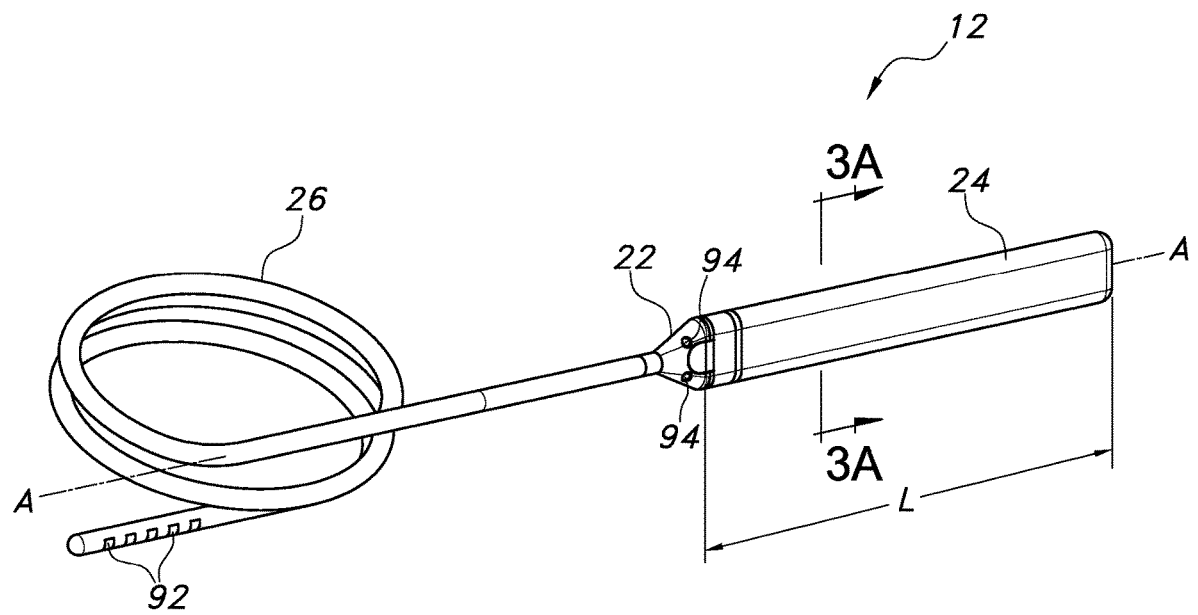
FIG. 3 is a perspective view comprising a header assembly 22 according to the present invention that detachably connects between an exemplary active implantable medical device (AMD) 12 and an implantable lead 26.
Figure 3A:
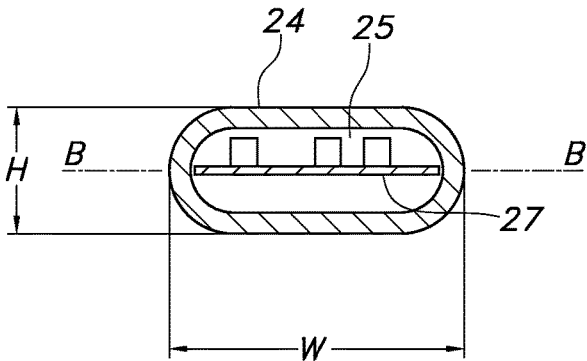
FIG. 3A is a cross-sectional view taken along line 3A-3A of FIG. 3.
Figure 4:
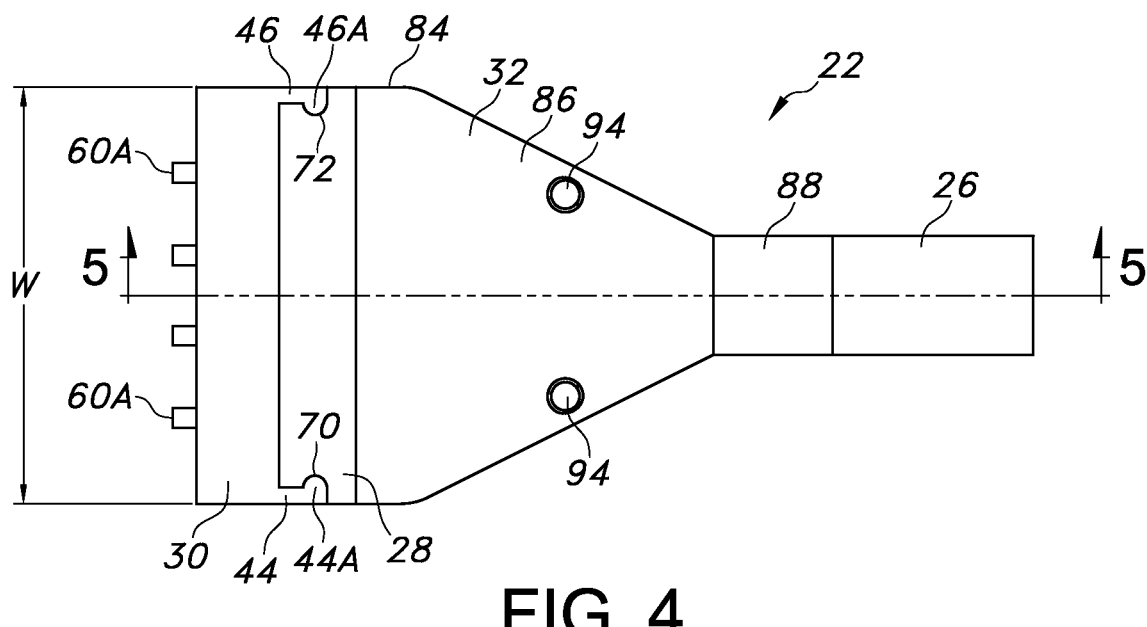
FIG. 4 is a plan view of one embodiment of a header assembly 22 for the AMD 12 shown in FIG. 3.

Referring now to FIGS. 3 and 3A, these drawings illustrate the AMD 12 as an exemplary embodiment of the various medical devices 100A to 100L illustrated in FIG. 1 and the exemplary AMD 12 shown in the medical device system 10 (FIG. 2) that can be implanted in a patient's body or worn externally on a patient's body. The AMD 12 is shown as an elongate device that comprises a header assembly 22 connected to a device housing 24 and has an exemplary length L of about 15 mm extending along a longitudinal axis A-A, a width W of about 7 mm extending along a lateral axis B-B, and a cross-sectional height H of about 3 mm. According to the present invention, however, the shape of the AMD 12 is not limited to the elongate shape that is shown. For example, the AMD 12 could have a cylindrical shape or a shape that is not elongated.

The device housing 24 contains a printed circuit board (PCB) assembly comprising a PCB 25 supporting at least one electronic circuit or electronic component 27. The device housing 24 also contains an electrical power source (not shown) that is electrically connected to the PCB assembly to provide electrical power to the at least one electronic circuit or electronic component 27. The PCB assembly in turn provides electrical power to a lead 26 that is detachably connected to the header assembly 22. The lead 26 has a number of electrodes 92 that are configured to deliver current pulses to the body tissue, receive sensed electrical signals pertaining to functions of a body tissue in which the AMD 12 is implanted, or both sense electrical signals and deliver current pulses. Titanium is a preferred material for the device housing 24.

The electrical power source for the AMD 12 can be a capacitor or a rechargeable battery, for example a hermetically sealed rechargeable Li-ion battery. However, the electrical power source is not limited to any one chemistry or even a rechargeable chemistry and can be of an alkaline cell, a primary lithium cell, a rechargeable lithium-ion cell, a Ni/cadmium cell, a Ni/metal hydride cell, a supercapacitor, a thin film solid-state cell, and the like. Preferably, the electrical power source is a lithium-ion electrochemical cell comprising a carbon-based or $Li_4Ti_5O_{12}$-based anode and a lithium metal oxide-based cathode, such as of $LiCoO_2$ or lithium nickel manganese cobalt oxide ($LiNi_aMn_bCo_{1-a-b}O_2$). The electrical power source can also be a solid-state thin film electrochemical cell having a lithium anode, a metal-oxide based cathode and a solid electrolyte, such as an electrolyte of LiPON ($Li_xPO_yN_z$).

FIGS. 4 to 7 illustrate one embodiment of the header assembly 22 in greater detail. The header assembly 22 comprises a lead connector 28 that is positioned between a feedthrough 30 for the AMD 12 and a strain-relief device 32. The feedthrough 30 is welded into an opening in the housing 24 of the AMD 12 and the strain-relief device 32 is fixedly connected to the proximal end of the lead 26. The lead connector 28 is fixedly connected to the strain-relief device 32 but is detachably connectable to the feedthrough 30 for selectively connecting and disconnecting the lead 26 to and from the AMD 12.

The feedthrough 30 includes a ferrule 34 having an annular sidewall 36 surrounding an opening 38. The annular sidewall 36 has a height extending from a proximal or device side end surface 40 to a distal end surface or body fluid side end surface 42. A pair of spaced-apart arms 44 and 46 extend distally from the body fluid side end surface 42. The arms 44, 46 are provided with respective inwardly extending detents 44A and 46A. The ferrule 34 also has an inner annular step 48 (FIG. 5) extending part-way through its height from the body fluid side end surface 42. An annular groove 50 (FIG. 7) residing part-way between the step 48 and the body fluid side end surface 42 is sized to receive an O-ring 52. Ferrule 34 is preferably made of titanium.

A ceramic insulator 54 resides in the ferrule opening 38 where it is hermetically sealed to the ferrule 34 with a gold braze 56, as is well known by those skilled in the art of feedthrough assemblies. The insulator 54 has a number of vias 58 that extend through its thickness from a body fluid side to a device side thereof. While four vias 58 are shown, that is not a limitation of the present invention. There can be less than four vias, for example, one, two or three vias, or more than four vias, for example eight, 12, 24, or more vias, as a particular AMD 12 will require. Alumina is a suitable material for the insulator 54.

A like number of terminal pins 60 are hermetically sealed in a respective one of the vias 58 using a gold braze 59, as is well known by those skilled in the art. A length extending along a second longitudinal axis of each of the terminal pins 60 is aligned parallel to the longitudinal axis A-A of the device housing 24, and the terminal pins are arranged side-by-side along the lateral axis B-B (FIGS. 3 and 3A). In addition to being aligned parallel to the longitudinal axis A-A of the device housing 24, an imaginary extension of the second longitudinal axis of each of the terminal pins 60 extends into the device housing. Platinum is a suitable material for the terminal pins 60.

Each of the terminal pins 60 has a proximal or device side portion 60A connected to a cup-shaped distal or body fluid side portion 60B. The device side portion 60A of the terminal pin 60 is preferably cylindrically-shaped. With a terminal pin 60 brazed into a via 58 in the insulator 54, the device side portion 60A extends outwardly beyond the device side of the insulator 54 and the cup-shaped distal or body fluid side portion 60B extends outwardly beyond the body fluid side of the insulator.

The lead connector 28 is an electrically non-conductive member that is made from a polymeric material, for example, PEEK, and is fixedly connected to the strain-relief device 32. The lead connector 28 has an annular sidewall 62 extending from a device side end surface 64 to a body fluid side end surface 66. A protruding rim 68 is spaced inwardly from an outer surface of the annular sidewall 62 and extends proximally from the device side end surface 64 of the lead connector 28. The protruding rim 68 surrounds a number of dividing walls 74 that together with the rim 68 form a plurality of open compartments 76 corresponding to the number of terminal pins 60 in the feedthrough 30.

The lead connector 28 also has spaced apart lateral recesses 70 and 72 in its annular sidewall 62. These recesses 70, 72 receive the detents 44A, 46A of the ferrule extending arms 44, 46 to connect the lead connector 28 to the feedthrough 30.

Figure 5:
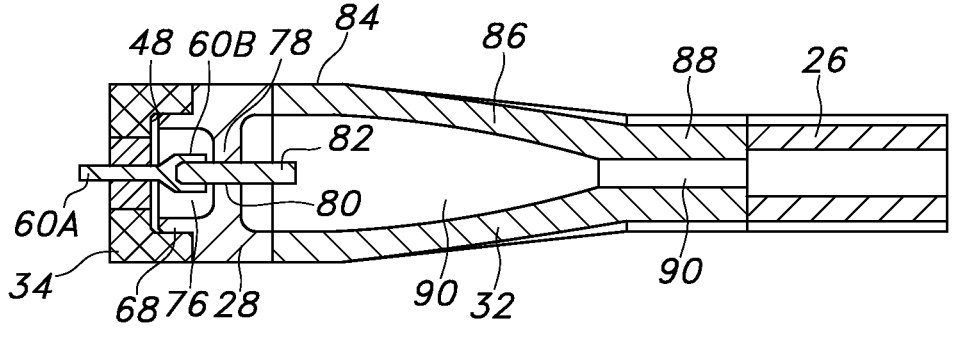
FIG. 5 is a cross-sectional view taken along line 5-5 of FIG. 4.
Figure 6:
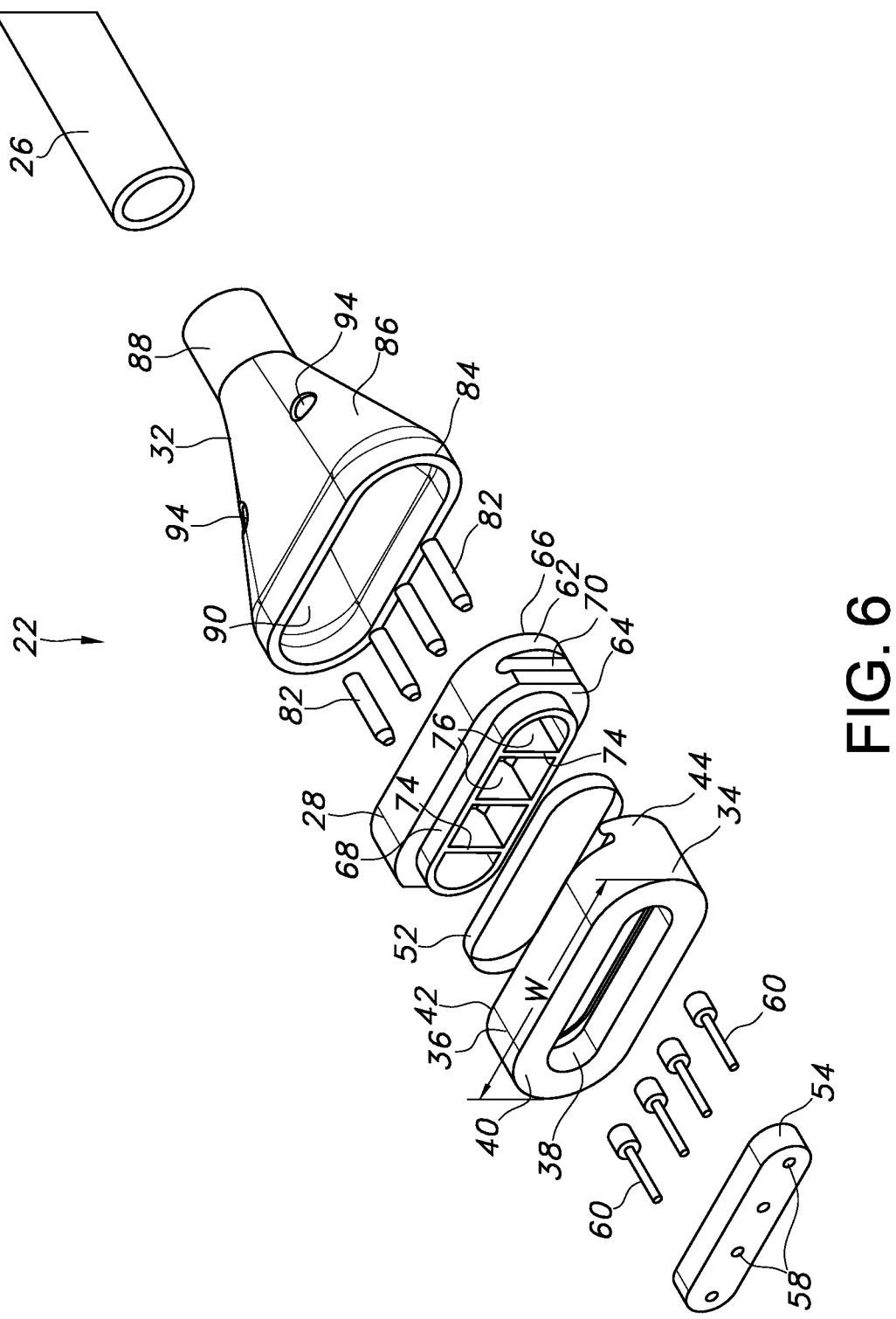
FIG. 6 is an exploded view of the header assembly 22 shown in FIGS. 4 and 5.
Figure 7:
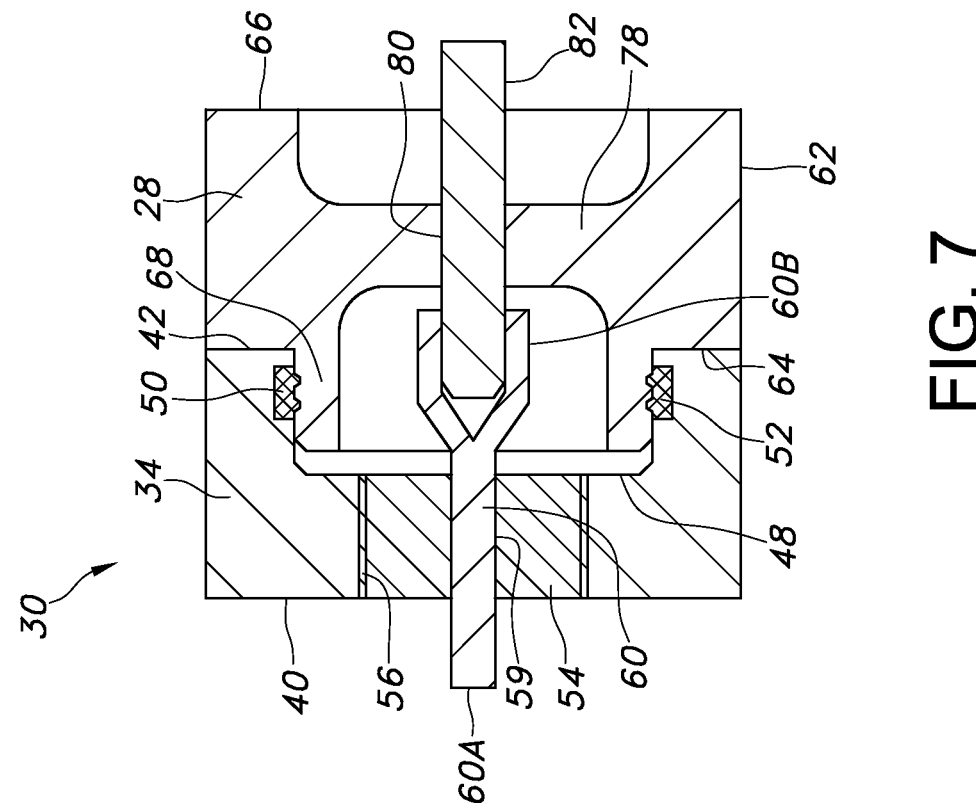
FIG. 7 is a cross-sectional view of a feedthrough 30 having an insulator 54 supporting a terminal pin 60 connected to a connector pin 82 of a lead connector 28 for the header assembly 22 shown in FIGS. 4 to 6.

As shown in FIGS. 5 and 7, a lateral web 78 resides between the device side and body fluid side end surfaces 64, 66 of the polymeric lead connector 28. The web 78 extends laterally across the dividing walls 74 forming the open connector compartments 76 and is provided with a plurality of connector openings 80 that correspond to the number of terminal pins 60 of the feedthrough 30. The connector openings 80 are sized to receive connector pins 82, each pin having a proximal or device side portion with a tapered nose extending outwardly beyond a device side of the web 78 and a distal or body fluid side portion extending outwardly beyond a body fluid side of the web. Platinum is a suitable material for the connector pins 82.

With the protruding rim 68 of the lead connector 28 seated in the annular step 48 of the ferrule 34, the detents 44A, 46A of the ferrule arms 44, 46 are received in the lateral recesses 70, 72 of the lead connector 28 to detachable mate the lead connector to the feedthrough 30. In this mated configuration, the tapered noses of the device side portion of the connector pins 82 are received in a snug fitting relationship and electrically connected to the cup-shaped body fluid side portions 60B of the terminal pins 60 of the feedthrough 30. That way, the longitudinal axis of the first and second terminal pins connected to the respective first and second connector pins are aligned parallel to the longitudinal axis of the device housing. Moreover, imaginary extensions of the longitudinal axes of the first and second terminal pins connected to the respective first and second connector pins extend into the device housing. This connection provides electrical continuity from the proximal or device side portion 60A of the terminal pins 60 located inside the AMD 12 where they are connected to the electronic circuits 27 (FIG. 3A) housed inside the medical device to the distal or body fluid side portion of the connector pins 82 extending outwardly beyond the body fluid side of the lateral web 78. The O-ring 52 helps prevent ingress of body fluids, and the like, to the electrical connection of the terminal pins 60 to the connector pins 82 with the feedthrough 30 mated to the lead connector 28.

The strain-relief device 32 is a one-piece member comprising a proximal annular sidewall 84 that joins to an intermediate annularly bevel-shaped sidewall 86. The beveled sidewall 86 extends distally as it narrows to join a cylindrically-shaped sleeve 88. A lumen 90 extends through the strain-relief device 32. A proximal face of the annular sidewall 84 is bonded to the body fluid side end surface 66 of the lead connector 28, for example, with an adhesive or by ultrasonic welding. The strain-relief device 32 is made from a polymeric material, for example, PEEK.

The strain-relief lumen 90 houses a plurality of electrical conductors (380 in FIGS. 15 to 18) of the lead 26. The proximal ends of the lead electrical conductors are connected to a respective one of the connector pins 82 of the lead connector 28. The distal ends of the lead electrical conductors are electrically connected to a lead electrode 92 (FIG. 3), as is well known by those skilled in the art. That way, with the strain-relief device 32 joined to the lead connector 28 and with the lead connector detachably connected to the feedthrough 30, there is electrical continuity from the electronic circuits or components 27 (FIG. 3A) housed inside the AMD 12 to a terminal pin 60 of the feedthrough 30 connected to a connector pin 82 of the lead connector 28 connected to an electrical conductor of the lead 26 to a lead electrode 92. The strain-relief device 32 is also provided with spaced-apart suture openings 94 that are sized to receive a suture during a medical procedure to secure the header assembly 22 to body tissue, as is well known by those skilled in the art.

Figure 8:
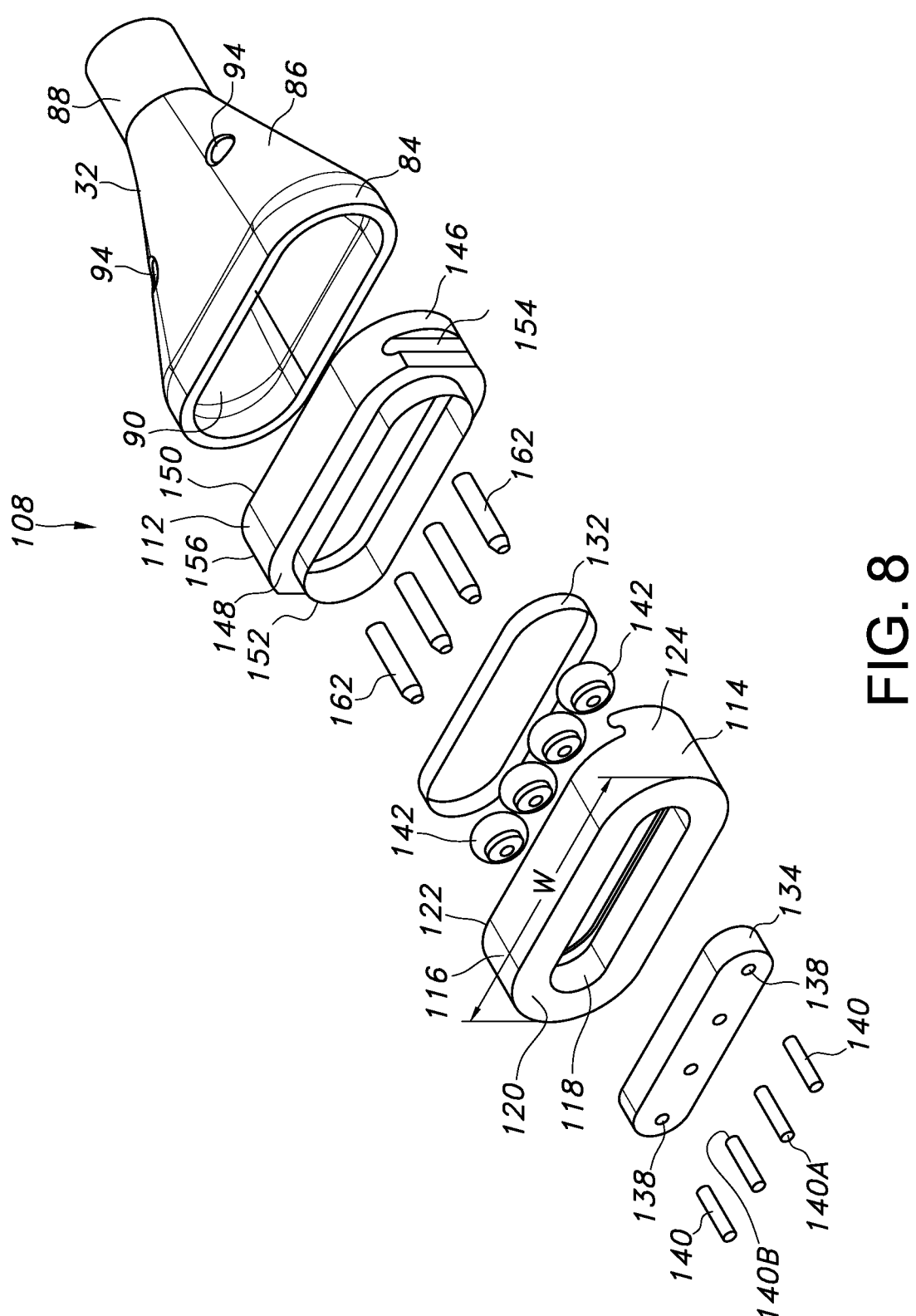
FIG. 8 is an exploded view of another embodiment of a header assembly 108 according to the present invention.
Figure 9:
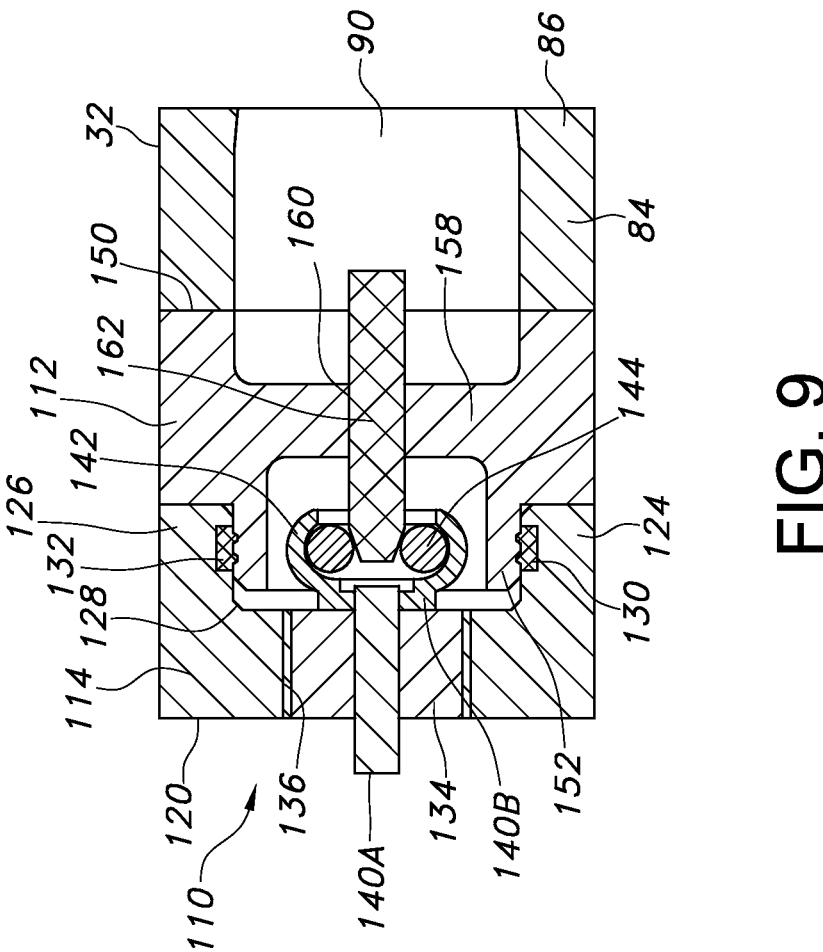
FIG. 9 is a cross-sectional view of a feedthrough 110 having an insulator 134 supporting a terminal pin 140 connected to a connector pin 162 of a lead connector 112 for the header assembly 108 shown in FIG. 8.
Figure 10:
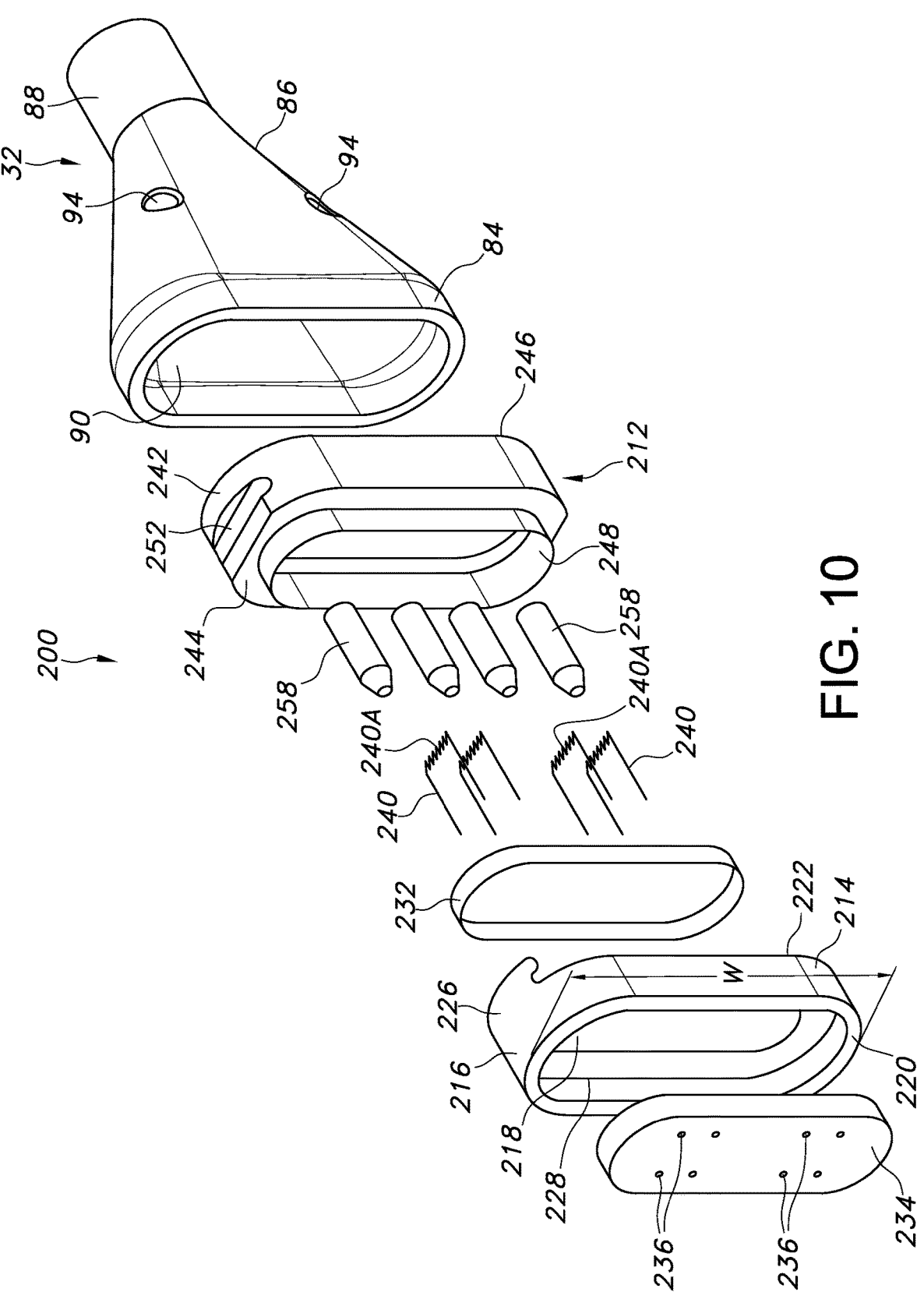
FIG. 10 is an exploded view of another embodiment of a header assembly 200 according to the present invention.

FIGS. 8 and 9 illustrate another embodiment of a header assembly 108 according to the present invention. The header assembly 108 has a feedthrough 110 that is detachably connected to a lead connector 112 and a strain-relief device 32 subassembly.

In a similar manner as the feedthrough 30 shown in FIGS. 4 to 7, feedthrough 110 includes a ferrule 114 having an annular sidewall 116 surrounding an opening 118. The annular sidewall 116 has a height extending from a proximal or device side end surface 120 to a distal or body fluid side end surface 122. A pair of spaced-apart arms 124 and 126 extend distally from the body fluid side end surface 122. The arms 124, 126 are provided with respective inwardly extending detents (not shown). The ferrule 114 also has an inner annular step 128 extending part-way through its height from the body fluid side end surface 122. An annular groove 130 residing part-way between the step 128 and the body fluid side end surface 122 is sized to receive an O-ring 132. Ferrule 114 is preferably made of titanium.

A ceramic insulator 134 resides in the ferrule opening 118 where it is hermetically sealed to the ferrule 114 with a gold braze 136. The insulator 134 has a number of vias 138 that extend through its thickness from a body fluid side to a device side thereof. While four vias 138 are shown, in a similar manner as the previously described insulator 54, that is not a limitation of the present invention. There can be less than or more than four vias, as a particular AMD 12 will require. Alumina is a suitable material for the insulator 134.

A like number of cylindrically-shaped terminal pins 140 are hermetically sealed in a respective one of the vias 138 using a gold braze, as is well known by those skilled in the art. A length extending along a second longitudinal axis of each of the terminal pins 140 is aligned parallel to the longitudinal axis A-A of the device housing 24, and the terminal pins are arranged side-by-side along the lateral axis B-B (FIGS. 3 and 3A). In addition to being aligned parallel to the longitudinal axis A-A of the device housing 24, an imaginary extension of the second longitudinal axis of each of the terminal pins 140 extends into the device housing. Platinum is a suitable material for the terminal pins 140.

Each of the terminal pins 140 has a proximal or device side portion 140A extending outwardly beyond the device side of the insulator 134 and a distal or body fluid side portion 140B extending outwardly beyond the body fluid side of the insulator. A cup-shaped, distally-facing metallic housing 142 is connected to the body fluid side portion 140B of the terminal pin 140. An annular spring 144 is nested in a respective one of the cup-shaped housings 142. A suitable annular spring 144 is a BAL SEAL® type canted coil spring (BAL SEAL is a registered trademark of Bal Seal Engineering Co., Inc.).

The polymeric (PEEK) lead connector 112 is an electrically non-conductive member that has an annular sidewall 146 extending from a device side end surface 148 to a body fluid side end surface 150. A protruding rim 152 is spaced inwardly from an outer surface of the annular sidewall 146 and extends proximally from the device side end surface 148 of the lead connector 112. The lead connector 112 also has spaced apart lateral recesses 154 and 156 in its annular sidewall 146. These lateral recesses 154, 156 receive the detents of the ferrule extending arms 124, 126 to detachably connect the lead connector 112 to the feedthrough 110.

As shown in FIG. 9, a lateral web 158 resides between the device side and body fluid side end surfaces 148, 150 of the polymeric lead connector 112. The web 158 is provided with a plurality of connector openings 160 that correspond to the number of terminal pins 140 of the feedthrough 110. The connector openings 160 are sized to receive connector pins 162, each pin having a proximal or device side portion with a tapered nose extending outwardly beyond a device side of the web 158 and a distal or body fluid side portion extending outwardly beyond a body fluid side of the web. Platinum is a suitable material for the connector pins 162.

With the protruding rim 152 of the connector seated in the annular step 128 of the ferrule 114, the detents of the ferrule arms 124, 126 are received in the lateral recesses 154, 156 of the lead connector 112 to mate the lead connector 112 to the feedthrough 110. The tapered noses of the device side portion of the connector pins 162 are received in a snug fitting relationship and electrically connected to the annular springs 144 nested in the cup-shaped housings 142 connected to the terminal pins 140 of the feedthrough 110. This connection provides electrical continuity from the device side portion 140A of the terminal pins 140 located inside the AMD 12 where they are connected to the electronic circuits or components 27 (FIG. 3A) housed inside the medical device to the body fluid side portion of the connector pins 162 extending outwardly beyond the body fluid side of the connector web 158. The O-ring 132 helps prevent ingress of body fluids, and the like, to the electrical connection of the terminal pins 140 to the connector pins 162 with the feedthrough 110 detachably mated to the lead connector 112.

In a similar manner as the previously described header assembly 22 shown in FIGS. 4 to 7, the strain-relief device 32 comprises a proximal annular sidewall 84 joined to an intermediate annularly bevel-shaped sidewall 86. The beveled sidewall 86 extends distally as it narrows to join a cylindrically-shaped sleeve 88. A lumen 90 extends through the strain-relief device 32. A proximal face of the annular sidewall 84 is bonded to the body fluid side end surface 66 of the lead connector 28, for example, with an adhesive or by ultrasonic welding. The strain-relief device 32 is made from a polymeric material, for example, PEEK.

The strain-relief lumen 90 houses a plurality of electrical conductors (380 in FIGS. 15 to 18) of the lead 26. The proximal ends of the lead electrical conductors are connected to a respective one of the connector pins 162 of the lead connector 112. The distal ends of the lead electrical conductors are electrically connected to a lead electrode 92 (FIG. 3), as is well known by those skilled in the art. That way, with the strain-relief device 32 fixedly connected to the lead connector 112 and with the lead connector detachably connected to the feedthrough 110, there is electrical continuity from the electronic circuits or components 27 (FIG. 3A) housed inside the AMD 12 to a terminal pin 140 of the feedthrough 110 connected to a connector pin 162 of the lead connector 112 connected to an electrical conductor of the lead 26 to a lead electrode 92. The strain-relief device 32 is also provided with spaced-apart suture openings 94 that are sized to receive a suture during a medical procedure to secure the header assembly 108 to body tissue, as is well known by those skilled in the art.

FIGS. 10 to 13 illustrate another embodiment of a header assembly 200 according to the present invention. The header assembly 200 includes a feedthrough 210 which is detachably connected to a lead connector 212, which in turn is fixedly connected to the previously described strain-relief device 32. In a similar manner as the ferrules 34 and 114 for the feedthroughs 30 and 110 shown in FIGS. 4 to 7 and FIGS. 8 and 9, respectively, feedthrough 210 includes a ferrule 214 having an annular sidewall 216 surrounding an opening 218. The annular sidewall 216 has a height extending from a proximal or device side end surface 220 to a distal or body fluid side end surface 222. A pair of spaced-apart arms 224 and 226 extend distally from the body fluid side end surface 222. The arms 224, 226 are provided with respective inwardly extending detents 224A and 226A. The ferrule 214 also has an annular step 228 extending inwardly, part-way through its height from the body fluid side end surface 222. An annular groove 230 residing part-way between the step 228 and the body fluid side end surface 222 is sized to receive an O-ring 232. Ferrule 214 is preferably made of titanium.

A ceramic insulator 234 resides in the ferrule opening 218 where it is hermetically sealed to the ferrule 214 with a gold braze 236. The insulator 234 has a number of via pairs 236 that extend through its thickness from a body fluid side to a device side thereof. Each pair of vias is aligned so that one opening is adjacent to a first long side of the ferrule 214 and a second opening is adjacent to an opposed second long side of the ferrule. While four via pairs 236 are shown in the drawings, in a similar manner as the previously described insulators 54 and 134, that is not a limitation of the present invention. There can be less than or more than four pair of vias, as a particular AMD 12 will require. Looking at the device side of the insulator 234, a blind bore 238 resides adjacent to each of the via pairs 236. Alumina is a suitable material for the insulator 234.

Each via pair 236 receives a feedthrough spring wire 240 comprising an intermediate spring 240A connected to spaced-apart legs that reside in a respective opening of a via pair 236, where the legs are hermetically sealed to the insulator 234 using a gold braze, as is well known by those skilled in the art. A length extending along a second longitudinal axis of each leg of the feedthrough spring wires 240 is aligned parallel to the longitudinal axis A-A of the device housing 24, and the feedthrough spring wires are arranged side-by-side along the lateral axis B-B (FIGS. 3 and 3A). In addition to being aligned parallel to the longitudinal axis A-A of the device housing 24, an imaginary extension of each leg of the feedthrough spring wires 240 extends into the device housing. Platinum is a suitable material for the feedthrough spring wires 240.

The intermediate spring 240A is aligned spaced from and parallel to the body fluid side end surface of the insulator 234 and adjacent to a respective blind bore 238. Each of the space-apart legs of a feedthrough spring wire 240 extends outwardly beyond the device side of the insulator 234 while the intermediate spring portion 240A extends outwardly beyond the body fluid side of the insulator.

The polymeric (PEEK) lead connector 212 is an electrically non-conductive member that has an annular sidewall 242 extending from a device side end surface 244 to a body fluid side end surface 246. A protruding rim 248 is spaced inwardly from an outer surface of the annular sidewall 242 and extends proximally from the device side end surface 244 of the lead connector 212. The lead connector 212 also has spaced apart lateral recesses 250 and 252 in its annular sidewall 242. These recesses 250, 252 receive the detents 224A, 226A of the ferrule extending arms 224, 226 to detachably connect the lead connector 212 to the feedthrough 210.

Figures 11, 12, 13:
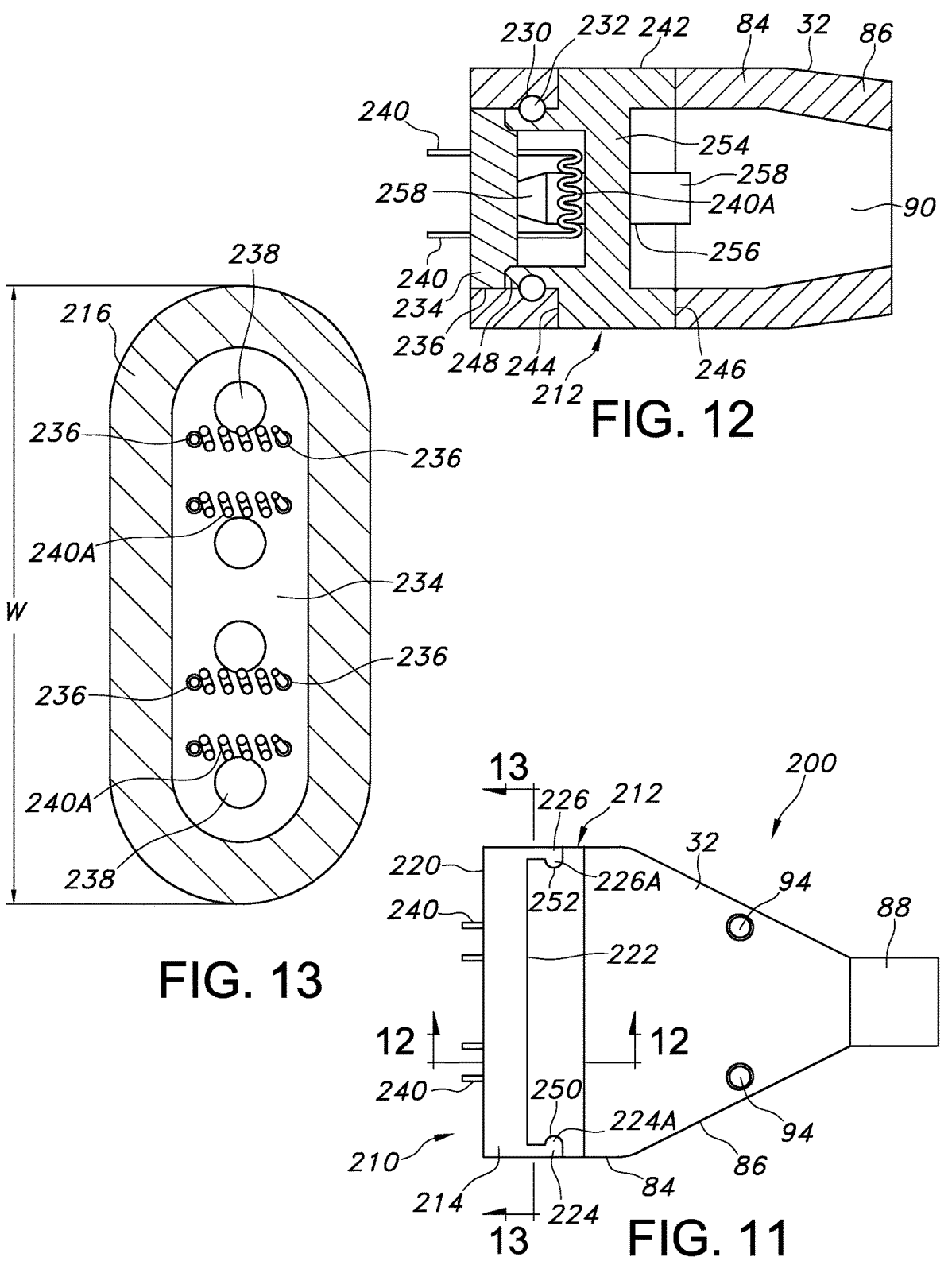
FIG. 11 is a plan view of the header assembly 200 shown in FIG. 10.
FIG. 12 is a cross-sectional view taken along line 12-12 of FIG. 11.
FIG. 13 is a cross-sectional view taken along line 13-13 of FIG. 11.

As shown in FIG. 12, a lateral web 254 resides between the device side and body fluid side end surfaces 244, 246 of the polymeric lead connector 212. The web 254 is provided with a plurality of connector openings 256 that correspond to the number of feedthrough spring wires 240 in the insulator 234. The connector openings 256 are sized to receive connector pins 258, each pin having a proximal or device side portion with a tapered nose extending outwardly beyond a device side of the connector web 254 and a distal or body fluid side portion extending outwardly beyond a body fluid side of the web. Platinum is a suitable material for the connector pins 258.

With the protruding rim 248 of the connector seated in the annular step 228 of the ferrule 214, the detents 224A, 226A of the ferrule arms 224, 226 are received in the lateral recesses 250, 252 of the lead connector 212 to detachably mate the lead connector 212 to the feedthrough 210. The device side portion of a connector pin 258 is now physically contacted to the intermediate spring 240A of a feedthrough spring wire 240 with the tapered node of the pin 258 extending into a blind bore 238 in the insulator 234. This connection provides electrical continuity from the device side portion of the spaced-apart legs of the feedthrough spring wire 240 located inside the AMD 12 where they are connected to the electronic circuits or components 27 (FIG. 3A) housed inside the medical device to the body fluid side portion of the connector pins 258 extending outwardly beyond the body fluid side of the connector web 254. The O-ring 232 helps prevent ingress of body fluids, and the like, to the electrical connection of the feedthrough spring wires 240 to the connector pins 258 with the feedthrough 210 detachably mated to the lead connector 212.

In a similar manner as the previously described header assemblies 22 and 200 shown in FIGS. 4 to 7 and FIGS. 8 and 9, respectively, the strain-relief device 32 comprises a proximal annular sidewall 84 joined to an intermediate annularly bevel-shaped sidewall 86. The beveled sidewall 86 extends distally as it narrows to join a cylindrically-shaped sleeve 88. A lumen 90 extends through the strain-relief device 32. A proximal face of the annular sidewall 84 is bonded to the body fluid side end surface 66 of the lead connector 28, for example, with an adhesive or by ultrasonic welding. The strain-relief device 32 is made from a polymeric material, for example, PEEK.

The strain-relief lumen 90 houses a plurality of electrical conductors (380 in FIGS. 15 to 18) of the lead 26. The proximal ends of the lead electrical conductors are connected to a respective one of the connector pins 258 of the lead connector 212. The distal ends of the lead electrical conductors are electrically connected to a lead electrode 92 (FIG. 3), as is well known by those skilled in the art. That way, with the strain-relief device 32 connected to the lead connector 212 and with the lead connector detachably connected to the feedthrough 210, there is electrical continuity from the electronic circuits or components 27 (FIG. 3A) housed inside the AMD 12 to a spring wire 240 of the feedthrough 110 connected to a connector pin 258 of the lead connector 212 connected to an electrical conductor of the lead 26 to a lead electrode 92. The strain-relief device 32 is also provided with spaced-apart suture openings 94 that are sized to receive a suture during a medical procedure to secure the header assembly 200 to body tissue, as is well known by those skilled in the art.

Figure 14:
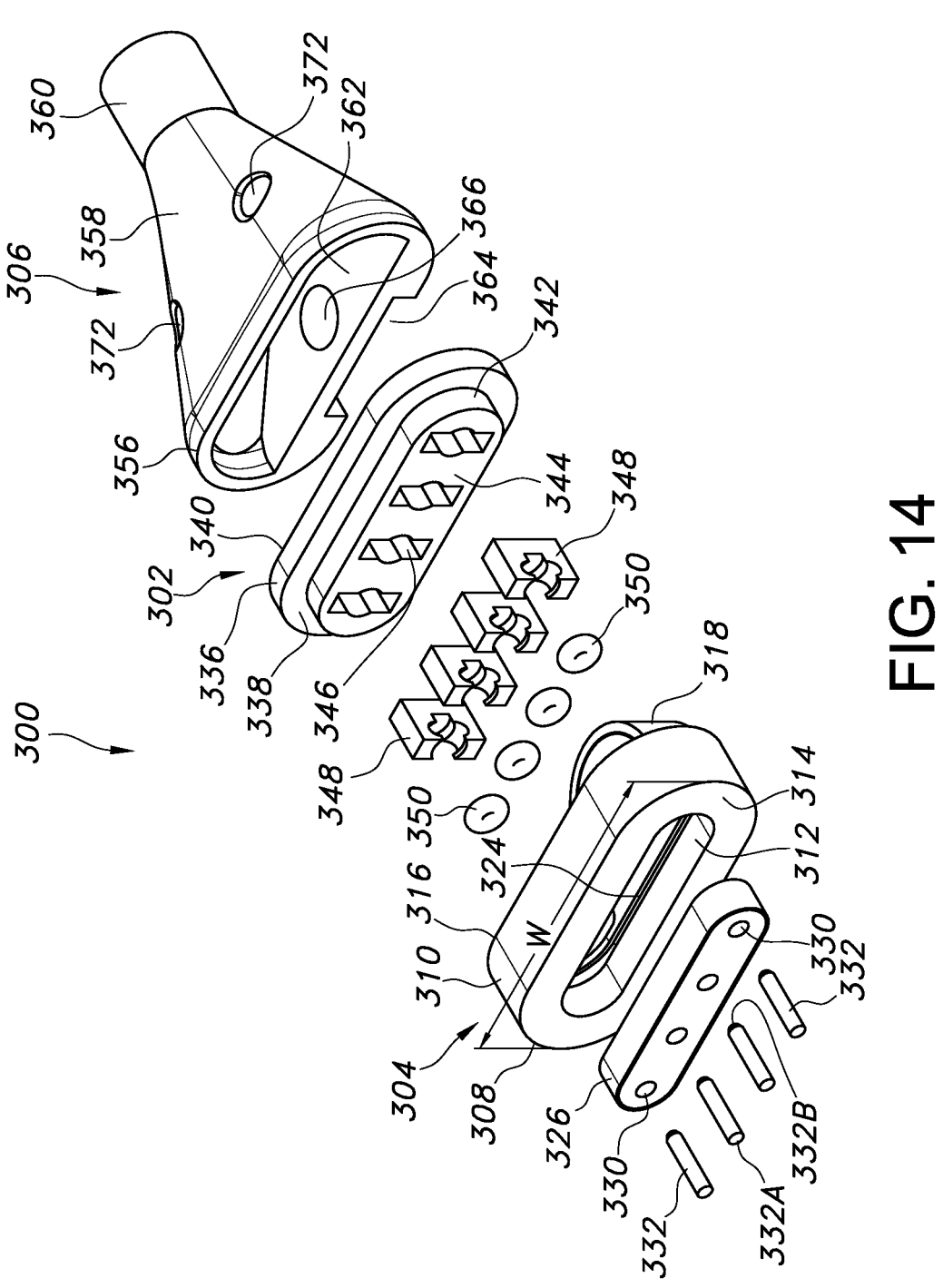
FIG. 14 is an exploded view of another embodiment of a header assembly 300 according to the present invention.
Figures 15, 16:
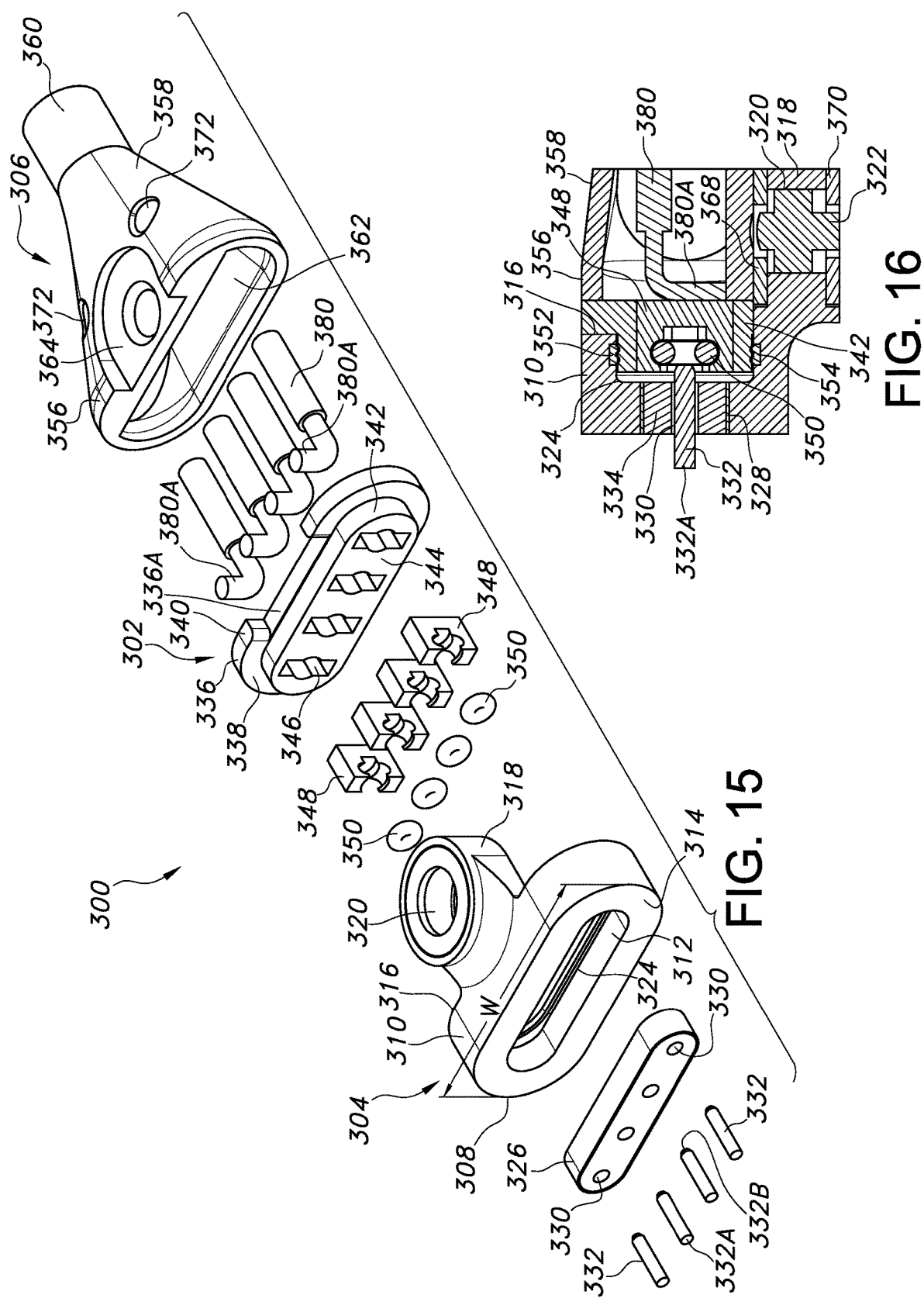
FIG. 15 is an exploded view of the header assembly 300 shown in FIG. 14, but from a different perspective.
FIG. 16 is a cross-sectional view of a feedthrough 304 having an insulator 326 supporting a terminal pin 332 connected to an annular spring 350 supported by a metallic insert 348 with a conductor 380 of a lead connected to the insert.

FIGS. 14 to 16 illustrate another embodiment of a header assembly 300 according to the present invention. The header assembly 300 comprises a lead connector 302 that is positioned between a feedthrough 304 for the AMD 12 and a strain-relief device 306. The feedthrough 304 is welded into an opening in the housing 24 of the AMD 12. The lead connector 302 is supported by the strain-relief device 306 and this subassembly 302/306 is fixedly connected to the proximal end of the lead 26. In turn, the strain-relief device 306 supporting the lead connector 302 is detachably connected to the feedthrough 304 for selectively connecting and disconnecting the lead 26 to and from the AMD 12 through the feedthrough 304.

The feedthrough 304 includes a ferrule 308 having an annular sidewall 310 surrounding an opening 312. The annular sidewall 310 has a height extending from a proximal or device side end surface 314 to a distal or body fluid side end surface 316. A centrally located hub 318 extends distally from the body fluid side end surface 314 of the annular sidewall 310. The hub 318 has a threaded opening 320 that receives a threaded member 322, for example, a set screw. The ferrule 308 also has an inner annular step 324 extending part-way through its height from the body fluid side end surface 316. Ferrule 308 is preferably made of titanium.

A ceramic insulator 326 resides in the ferrule opening 312 where it is hermetically sealed to the ferrule 308 with a gold braze 328, as is well known by those skilled in the art of feedthrough assemblies. The insulator 326 has a number of vias 330 that extend through its thickness from a body fluid side to a device side thereof. While four vias 330 are shown, in a similar manner as the previously described insulators 54, 134 and 234, that is not a limitation of the present invention. There can be less than or more than four vias, as a particular AMD 12 will require. Alumina is a suitable material for the insulator 326.

A like number of terminal pins 332 are hermetically sealed in a respective one of the vias 330. This is done using a gold braze 334, as is well known by those skilled in the art. A length extending along a second longitudinal axis of each of the terminal pins 332 is aligned parallel to the longitudinal axis A-A of the device housing 24, and the terminal pins are arranged side-by-side along the lateral axis B-B (FIGS. 3 and 3A).

Each of the terminal pins 332 has a cylindrically-shaped proximal or device side portion 332A connected to a distal or body fluid side portion 332B. With a terminal pin 332 brazed into a via 330 in the insulator 326, its cylindrically-shaped device side portion 332A extends outwardly beyond the device side of the insulator 326 and its body fluid side portion 332B extends outwardly beyond the body fluid side of the insulator.

The lead connector 302 is an electrically non-conductive member that is made from a polymeric material, for example, PEEK, and has an annular sidewall 336 extending from a device side end surface 338 to a body fluid side end surface 340. The annular sidewall has a recess 336A that is sized to receive the hub 318 extending from the ferrule 310 when the feedthrough 304 is connected to the strain-relief device 306, as will be described in greater detail hereinafter.

A protruding rim 342 is spaced inwardly from an outer surface of the annular sidewall 336 and extends proximally from the device side end surface 338 of the lead connector 302. The protruding rim 342 surrounds a number of dividing walls 344 that together with the rim 342 form a plurality of openings or compartments 346 corresponding to the number of terminal pins 332 in the feedthrough 304.

A proximally-facing metallic C-shaped insert 348 resides in each of the compartments 346. Each insert 348 supports a metallic annular spring 350 that is sized to receive the body fluid side portion 332B of a terminal pin 332. A suitable annular spring 350 is a BAL SEAL® type canted coil spring (BAL SEAL is a registered trademark of Bal Seal Engineering Co., Inc.).

The number of metallic inserts 348 and associated annular springs 350 corresponds to the number of terminal pins 332 of the feedthrough 304. With the protruding rim 342 of the lead connector 302 seated in the annular step 324 of the ferrule 308, the body fluid side portion 332B of the feedthrough terminal pins 332 are received in a snug fitting relationship and electrically connected to the annular springs 350 supported by the C-shaped inserts 348 of the lead connector 302. This connection provides electrical continuity from the device side portion 332A of the terminal pins 332 connected to the electronic circuits or components 27 (FIG. 3A) housed inside the AMD 12 to the metallic annular springs 350 supported by the metallic C-shaped inserts 348 of the lead connector 302. An O-ring 352 seated in an annular groove 354 in the ferrule 308 helps prevent ingress of body fluid, and the like, to the electrical connection of the terminal pins 332 to the annular springs 350 with the feedthrough 304 mated to the lead connector 302.

The strain-relief device 306 is a one-piece member comprising a proximal annular sidewall 356 that joins to the intermediate annularly bevel-shaped sidewall 358. The beveled sidewall 358 extends distally as it narrows to join a cylindrically-shaped sleeve 360. A lumen 362 extends through the strain-relief device 306. The strain-relief device 306 is made from a polymeric material, for example, PEEK.

The strain-relief device 306 also includes an inlet 364 extending inwardly from the proximal annular sidewall 356 into the beveled sidewall 358. The inlet 364 has a threaded opening 366 that is sized to receive the hub 318 of the ferrule 308 with the hub 318 extending through the recess 336A in the annular sidewall 336 of the lead connector 302 to connect the feedthrough 304 to the strain-relief device 306. This connection is secured by a first retention washer 368 that is nested in the threaded opening 366 followed by the threaded member 322 threaded into the opening 320 in the ferrule hub 318 and the opening 366 in the strain-relief device 306. A second retention washer 370 is seated on top of the threaded member 322. The strain-relief device 306 is also provided with spaced-apart suture openings 372 that are sized to receive a suture during a medical procedure to secure the header assembly 300 to body tissue, as is well known by those skilled in the art.

The strain-relief lumen 360 houses a plurality of electrical conductors 380 of the lead 26. The proximal end 380A of an electrical conductor 380 is bent at about a 90° angle so that it is aligned with a planar distal face of the insert 348. The proximal conductor end 380A is then secured to the insert 348, preferably with a weld (not shown). The distal end of the electrical conductor 380 is electrically connected to a lead electrode 92 (FIG. 3), as is well known by those skilled in the art. That way, with the protruding rim 342 of the lead connector 302 seated in the annular step 324 of the ferrule 308 and with the lead connector 302/strain-relief device 306 subassembly connected to the feedthrough 304 with the threaded member 322 threaded into the openings 320, 366 in the ferrule hub 318 and the strain-relief device 306, there is electrical continuity from the electronic circuits or components 27 (FIG. 3A) housed inside the AMD 12 to a terminal pin 332 of the feedthrough 304 connected to an annular spring 350 supported by the metallic insert 348 of the lead connector 302 connected to an electrical conductor 380 of the lead 26 to a lead electrode 92.

Figures 17, 18:
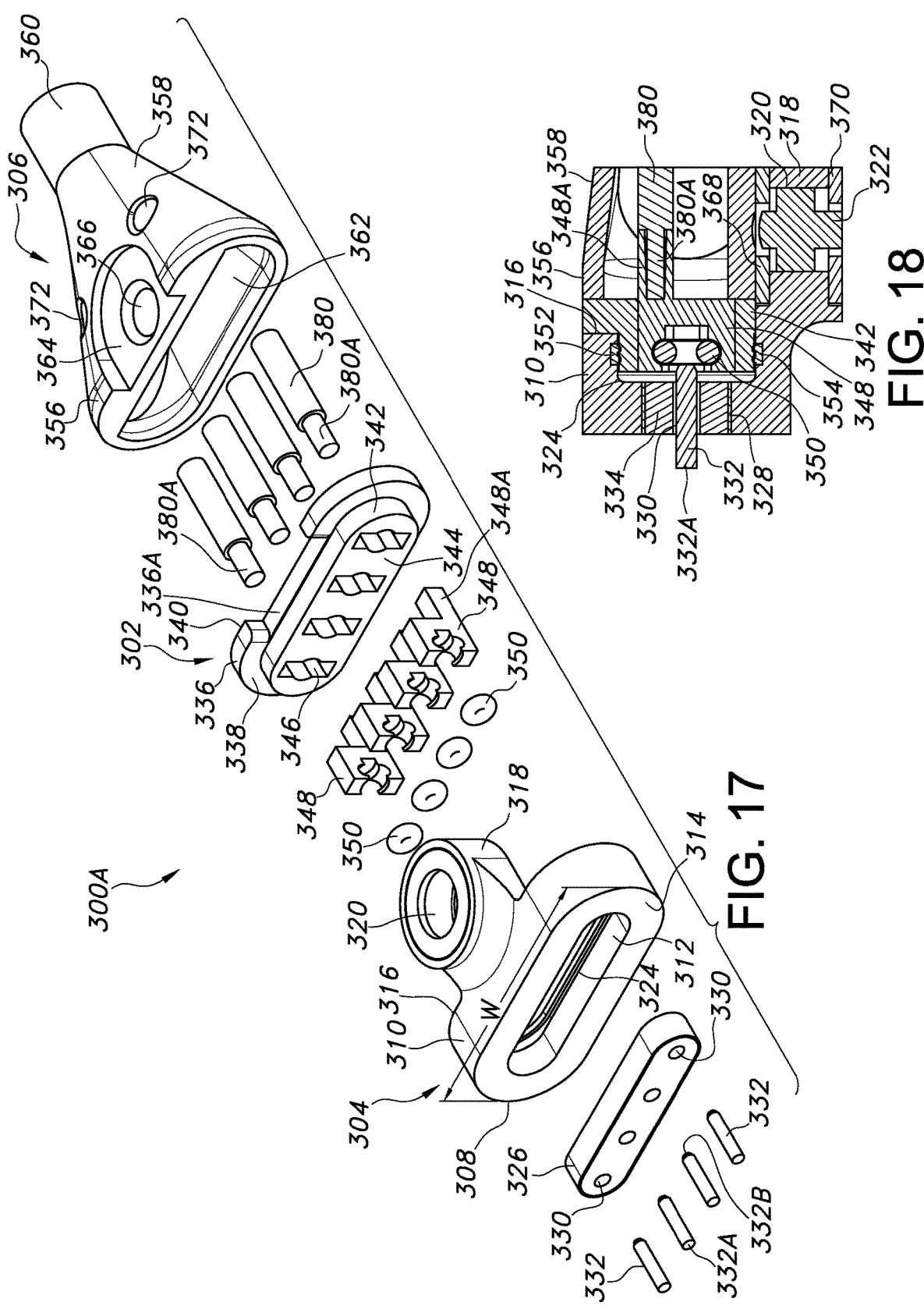
FIG. 17 is an exploded view of another embodiment of a header assembly 300A according to the present invention.
FIG. 18 is a cross-sectional view of a feedthrough 304 having an insulator 326 supporting a terminal pin 332 connected to an annular spring 350 supported by a metallic insert 348 with a conductor 380 of a lead 26 received in the bore of a distal extension 348A of the insert.

The header assembly 300A illustrated in FIGS. 17 and 18 is similar to the header assembly 300 shown in FIGS. 14 to 16 with the exception of the metallic C-shaped inserts 348. In this embodiment of a header assembly 300A according to the present invention, the metallic C-shaped inserts 348 have a distal extension 348A. Each insert 348 supports a metallic annular spring 350 that is sized to receive the body fluid side portion 332B of a terminal pin 332 with the number of inserts 348 and associated annular springs 350 corresponding to the number of terminal pins 332 of the feedthrough 304. A suitable annular spring 350 is a BAL SEAL® type canted coil spring (BAL SEAL is a registered trademark of Bal Seal Engineering Co., Inc.). Then, with the protruding rim 342 of the lead connector 302 seated in the annular step 324 of the ferrule 308, the body fluid side portion 332B of the feedthrough terminal pin 332 is received in a snug fitting relationship and electrically connected to the annular spring 350 supported by the C-shaped insert 348 of the lead connector 302. This connection provides electrical continuity from the device side portion 332A of the terminal pin 332 connected to the electronic circuits or components 27 (FIG. 3A) housed inside the AMD 12 to the metallic annular spring 350 supported by the metallic C-shaped insert 348 of the lead connector 302. The O-ring 352 seated in an annular groove 354 in the ferrule 308 helps prevent ingress of body fluid, and the like, to the electrical connection of the terminal pins 332 to the annular springs 350 with the feedthrough 304 mated to the lead connector 302.

The strain-relief lumen 360 houses a plurality of electrical conductors 380 of the lead 26. The proximal end 380A of a lead electrical conductor 380 is axially aligned with the rest of the conductor. The proximal conductor end 380A is then received in a bore in the distal extension 348A of a metallic insert 348. This connection is preferably secured with a weld (not shown). The distal end of the electrical conductor 380 is electrically connected to a lead electrode 92 (FIG. 3), as is well known by those skilled in the art. That way, with the protruding rim 342 of the lead connector 302/stain-relief 306 subassembly seated in the annular step 324 of the ferrule 308 and with the strain-relief device 306 connected to the feedthrough 304 with the threaded member 322 threaded into the openings 320, 366 in the ferrule hub 318 and the strain-relief device 306, there is electrical continuity from the electronic circuits or components 27 (FIG. 3A) housed inside the AMD 12 to a terminal pin 332 of the feedthrough 304 connected to an annular spring 350 supported by the metallic insert 348 of the lead connector 302 connected to an electrical conductor 380 of the lead 26 to a lead electrode 92.

FIGS. 19 to 22 illustrate an alternate embodiment for threadingly connecting the feedthrough 304 to the lead connector 302/strain-relief device 306 subassembly. However, while the lead connector 302 is not shown in these drawings, that is purely for the sake of simplicity. It is understood that a lead connector is an integral part of the various header assemblies of the present invention.

In a similar manner as previously described with respect to the header assemblies 300 and 300A shown in FIGS. 14 to 18, the strain-relief device 306 includes an inlet 372 extending inwardly from the proximal annular sidewall 356 into the beveled sidewall 358. However, the inlet 372 has a channel 373 that leads to an off-center spiral cavity 374 terminating at an edge 376. The terminal edge 376 is spaced closer to the proximal annular sidewall 356 than the rest of the spiral cavity 374.

Figures 19, 20, 21:
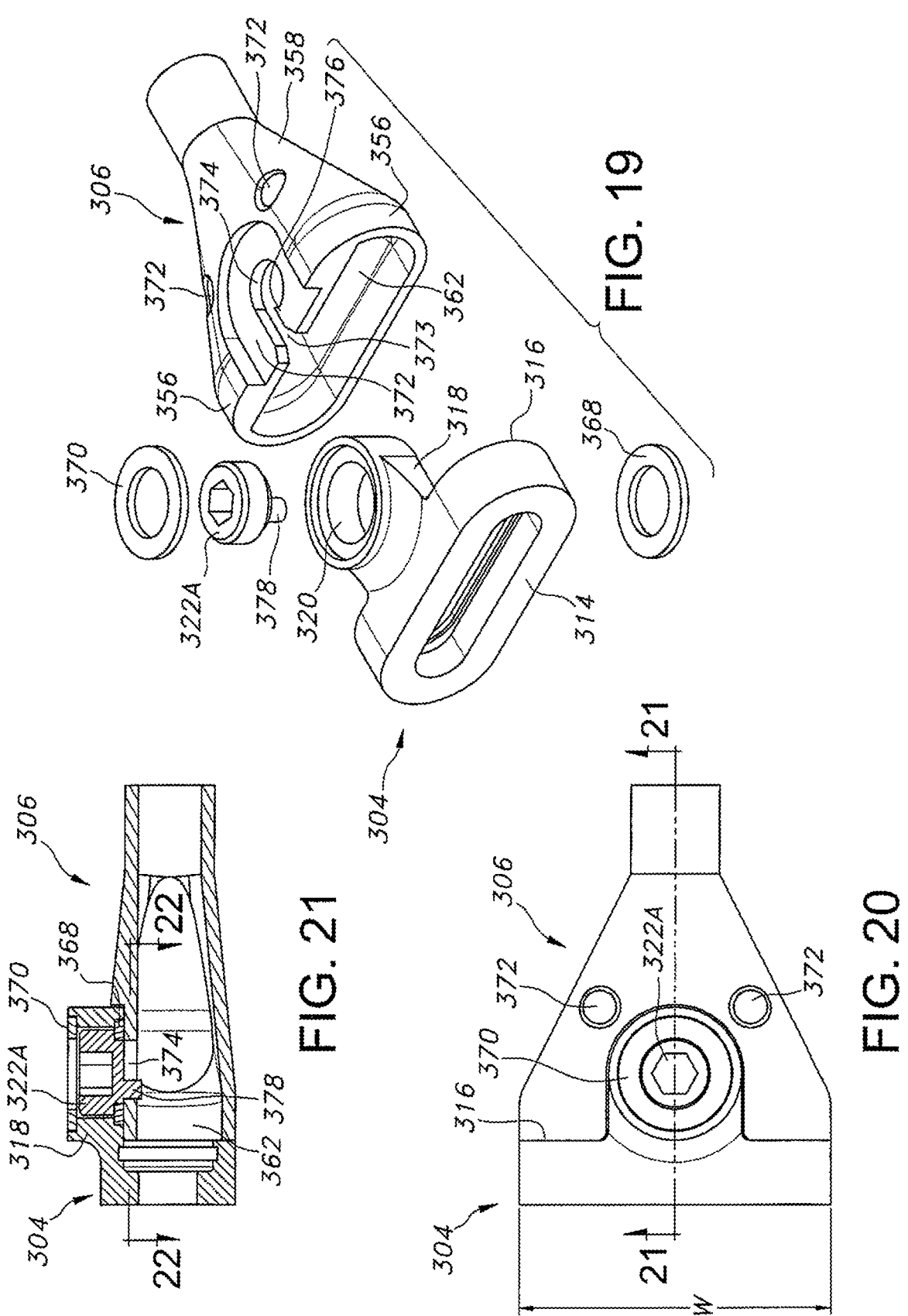
FIG. 19 is an exploded view of an alternate embodiment for threadingly connecting the feedthrough 304 to the strain-relief device 306 of the header assembly 300A shown in FIGS. 17 and 18.
FIG. 20 is a plan view of the feedthrough 304 connected to the strain-relief device 306 shown in FIG. 19.
FIG. 21 is a cross-sectional view of the feedthrough 304 connected to the strain-relief device 306 shown in FIGS. 19 and 20.
Figure 22:
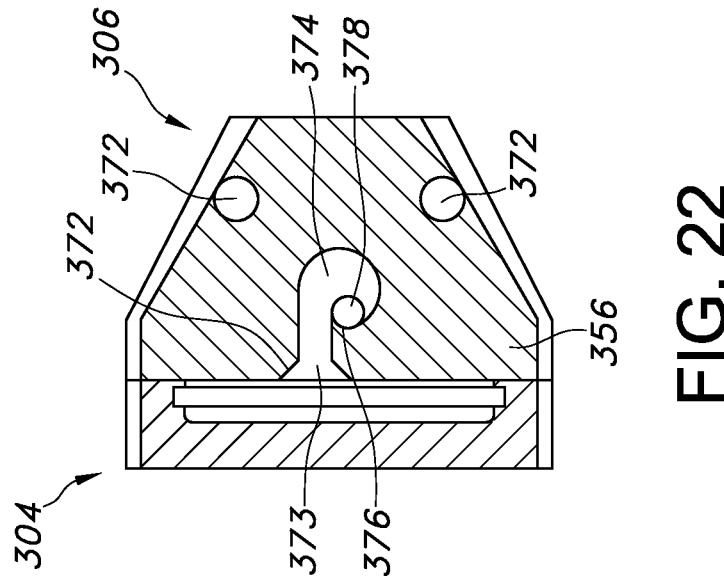
FIG. 22 is a cross-sectional view taken along line 22-22 of FIG. 21.
Figure 23:
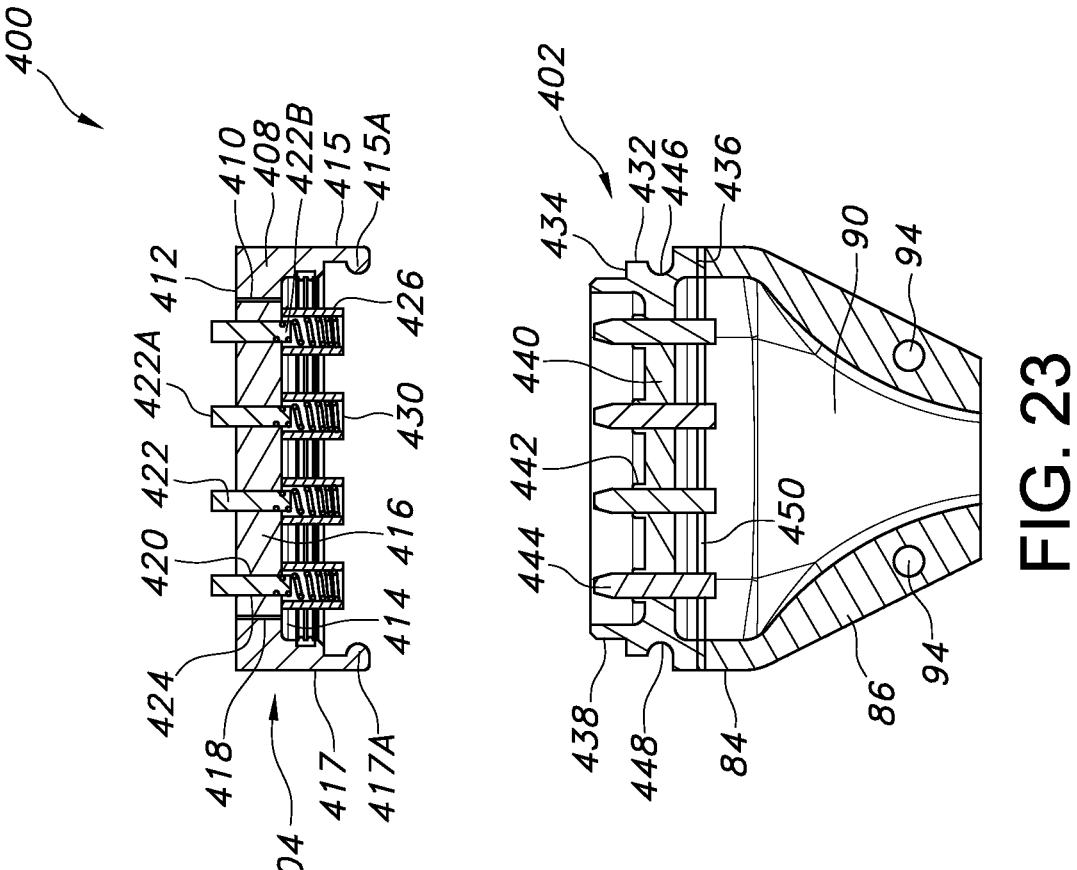
FIG. 23 illustrates another embodiment of a header assembly 400 according to the present invention with the feedthrough 404 separated from a strain-relief device 32/lead connector 402 subassembly.
Figure 24:
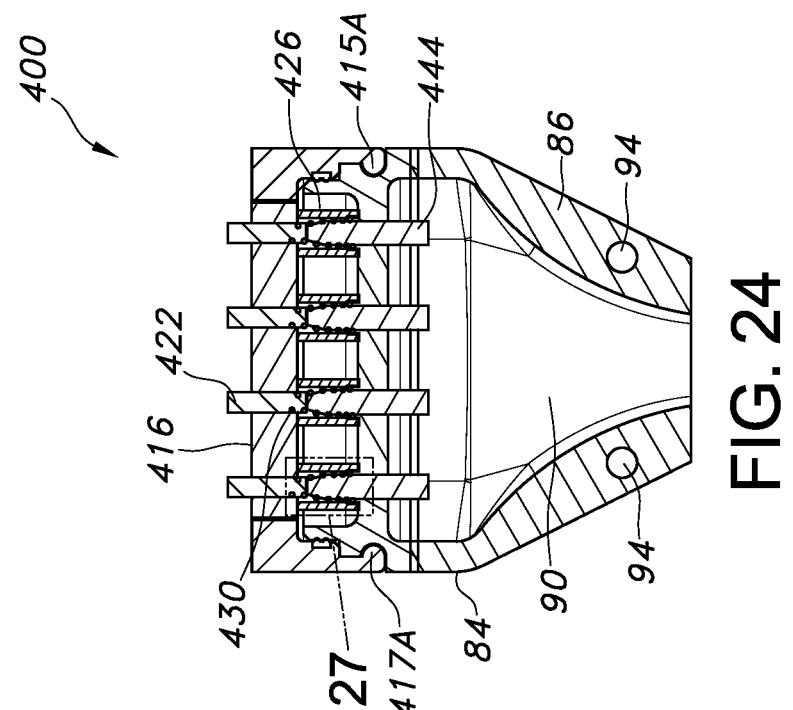
FIG. 24 shows the header assembly 400 of FIG. 23 with the feedthrough 404 connected to the strain-relief device 32/lead connector 402 subassembly.
Figures 25, 26:
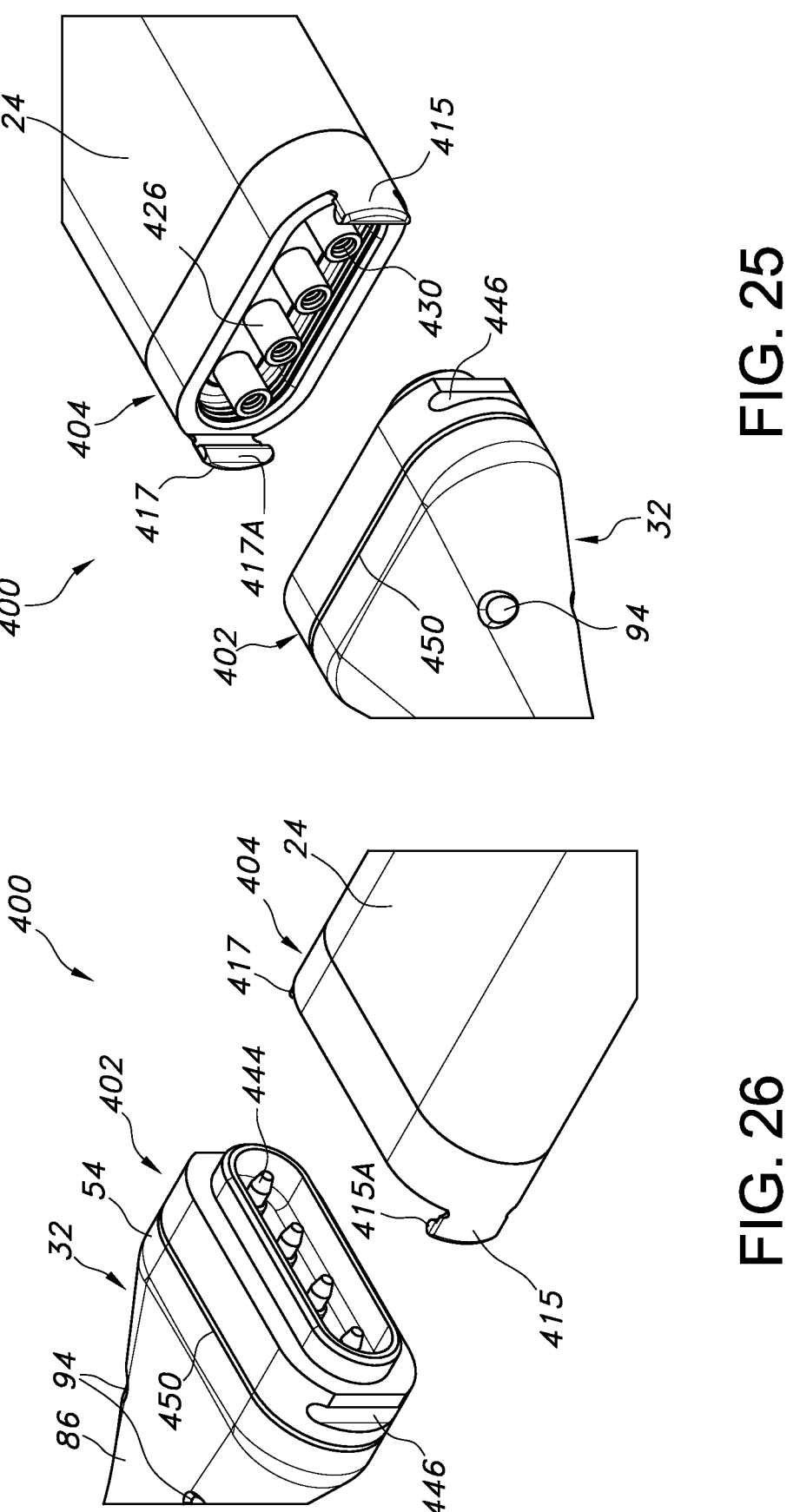
FIG. 25 illustrates the header assembly 400 shown in FIGS. 23 and 24 with the feedthrough 404 connected to the housing 24 of an AMD 12 and being separated from a strain-relief device 32/lead connector 402 subassembly.
FIG. 26 shows the header assembly 400 shown in FIG. 25 with the feedthrough 404 connected to the housing 24 of an AMD 12 and being connected to the strain-relief device 32/lead connector 402 subassembly.
Figure 27:
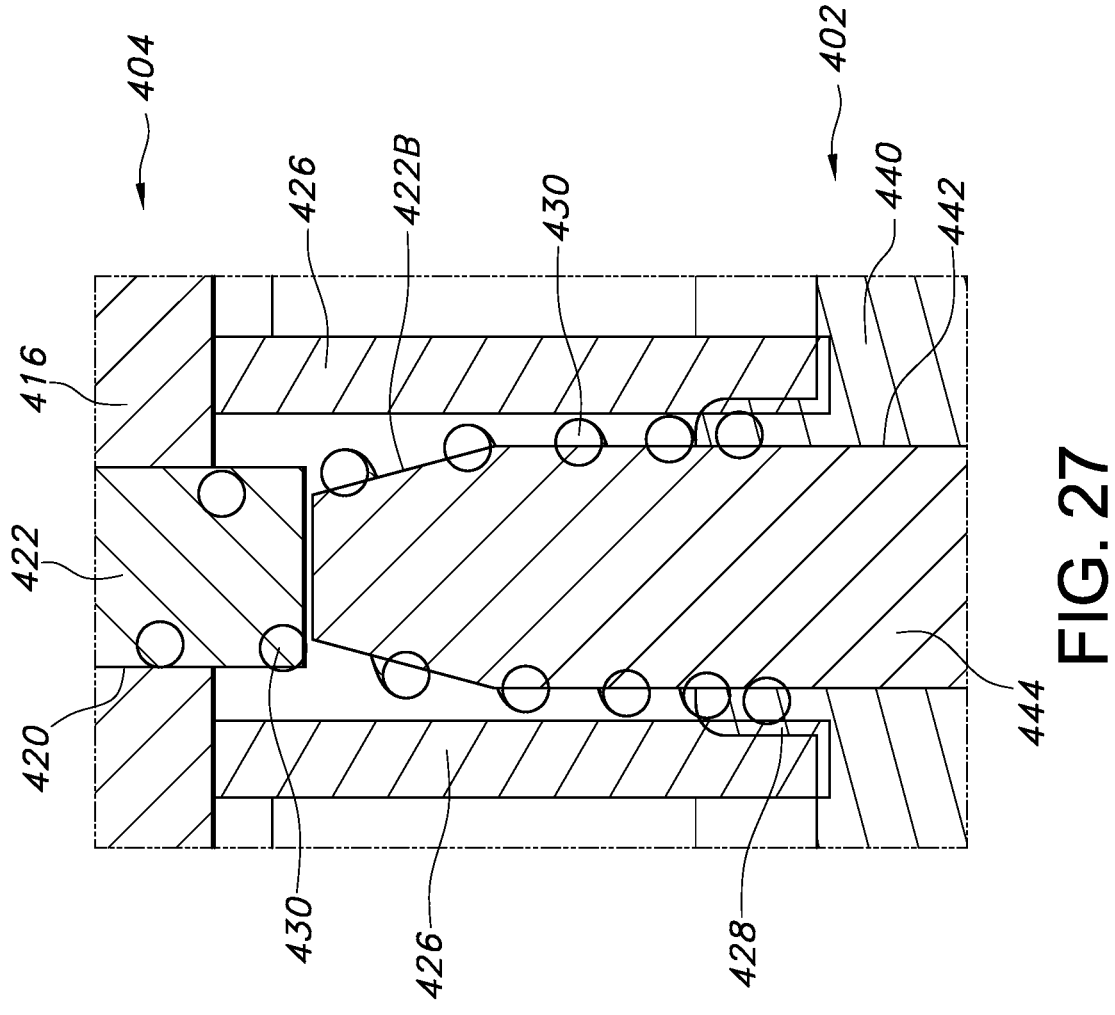
FIG. 27 is an enlarged view of the indicated area in FIG. 24 showing a connector pin 444 of the lead connector 402 electrically connected to a terminal pin 422 and associated sleeve 426/coil spring 430 subassembly of the feedthrough 404 for the header assembly 400 shown in FIGS. 23 to 26.

In this embodiment, the screw 322A is similar to the treaded member 322 shown in FIG. 19 except that it is devoid of threads, instead having a depending eccentric pin 378. Screwing the screw 322A into the opening 320 in the ferrule hub 318 and into the channel 373 and its spiral cavity 374 in the strain-relief device 306 causes the eccentric pin 378 to travel along the perimeter of the spiral cavity 374 until it seats at the terminating edge 374. This movement causes the lead connector 302 (not shown in FIGS. 19 to 21) connected to the strain-relief device 306 to move into an abutting relationship with the body fluid side end surface 316 of the feedthrough 304. That way, with the protruding rim 342 of the lead connector 302 seated in the annular step 324 of the ferrule 308 and with the screw 322A connecting the strain-relief device 306 to the feedthrough 304, there is electrical continuity from the electronic circuits or components 27 (FIG. 3A) housed inside the AMD 12 to a terminal pin 332 of the feedthrough 304 connected to an annular spring 350 supported by the metallic insert 348 of the lead connector 302 connected to an electrical conductor of the lead 26 to a lead electrode 92.

FIGS. 23 to 27 illustrate another embodiment of a header assembly 400 according to the present invention. The header assembly 400 comprises a lead connector 402 that is positioned between a feedthrough 404 for the AMD 12 and the previously described strain-relief device 32. The feedthrough 404 is welded into an opening in the housing 24 of the AMD 12. The lead connector 402 is supported by the strain-relief device 32 and this subassembly 402/32 is fixedly connected to the proximal end of the lead 26. In turn, the strain-relief device 32 is detachably connected to the feedthrough 404 for selectively connecting and disconnecting the lead 26 to and from the AMD 12 through the feedthrough 404.

The feedthrough 404 includes a ferrule 408 having an annular sidewall surrounding an opening 410. The annular sidewall has a height extending from a proximal or device side end surface 412 to a distal or body fluid side end surface 414. Ferrule 408 is preferably made of titanium. A pair of spaced-apart arms 415 and 417 extend distally from the body fluid side end surface 414. The arms 415, 417 are provided with respective inwardly extending detents 415A and 417A. Titanium is a suitable material for the ferrule 408.

A ceramic insulator 416 resides in the ferrule opening 410 where it is hermetically sealed to the ferrule 408 with a gold braze 418, as is well known by those skilled in the art of feedthrough assemblies. The insulator 416 has a number of vias 420 that extend through its thickness from a body fluid side to a device side thereof. While four vias 420 are shown, in a similar manner as the previously described insulators 54, 134, 234 and 326, that is not a limitation of the present invention. There can be less than or more than four vias, as a particular AMD 12 will require. Alumina is a suitable material for the insulator 416.

A like number of terminal pins 422 are hermetically sealed in a respective one of the vias 420. This is done using a gold braze 424, as is well known by those skilled in the art. A length extending along a second longitudinal axis of each of the terminal pins 422 is aligned parallel to the longitudinal axis A-A of the device housing 24, and the terminal pins are arranged side-by-side along the lateral axis B-B (FIGS. 3 and 3A). In addition to being aligned parallel to the longitudinal axis A-A of the device housing 24, an imaginary extension of the second longitudinal axis of each of the terminal pins 422 extends into the device housing. Each of the terminal pins 422 is a cylindrically-shaped member having a proximal or device side portion 422A extending to a distal or body fluid side portion 422B. Platinum is a suitable material for the terminal pins 422.

A cylindrically-shaped sleeve 426 is also connected 428 to the insulator 416, surrounding the body fluid side portion 422B of the terminal pin 422. The sleeve 426 is made from a polymeric material, for example, silicone and is connected to the insulator using an adhesive 428, and the like.

A cylindrically-shaped coil spring 430 housed inside each sleeve 426 is connected to the body fluid side portion 422B of the terminal pin 422. The spring 430 tapers outwardly from the terminal pin 422 to adjacent to a distal end of the sleeve 426. With the terminal pin 422 brazed 428 into a via 420 in the insulator 416, its device side portion 422A extends outwardly beyond the device side of the insulator 416 and its body fluid side portion 422B connected to the coil spring 430 extends outwardly beyond the body fluid side of the insulator 416 and into the sleeve 426.

The lead connector 402 is an electrically non-conductive member that is made from a polymeric material, for example, PEEK, and has an annular sidewall 432 extending from a device side end surface 434 to a body fluid side end surface 436. A protruding rim 438 is spaced inwardly from an outer surface of the annular sidewall 432 and extends proximally from the device side end surface 434 of the lead connector 402. A plate-shaped web 440 resides between the device side and body fluid side end surfaces 434, 436 of the connector 402. The web 440 is provided with a number of connector openings 442. The connector openings 442 are sized to receive connector pins 444, each pin having a proximal or device side portion with a tapered nose extending outwardly beyond a device side of the web 440 and a distal or body fluid side portion extending outwardly beyond a body fluid side of the web. The number of connector pins 444 supported by the connector web 438 corresponds to the number of terminal pins 422 and associated sleeve 426/coil spring 430 subassemblies of the feedthrough 404.

The lead connector 402 also has spaced apart lateral recesses 446 and 448 in its annular sidewall 432. These recesses 446, 448 receive the detents 415A, 417A of the ferrule extending arms 415, 417 to connect the lead connector 402 to the feedthrough 404. In that manner, with the detents 415A, 417A of the ferrule extending arms 415, 417 received in the recesses 446, 448, the connector pins 444 of the lead connector 402 are received in and electrically connected to the coil springs 430 connected to the terminal pins 422 of the feedthrough 404. This connection provides electrical continuity from the device side portion 422A of the terminal pins 422 connected to the electronic circuits or components 27 (FIG. 3A) housed inside the AMD 12 to the coil springs 430 electrically connected to the connector pins 444 of the lead connector 402. An important aspect of this header assembly 440 of the present invention is that in a relaxed state without a connector pin 444 being inside the coil spring 430, the coil spring does not touch the inside of the sleeve 426. Instead, the spring 430 is free to move laterally inside the sleeve 426. This provides a self-aligning function should the connector pin 444 not be precisely aligned with a center axis of the coil spring 430. Instead, the connector pin can be somewhat out of perfect axial alignment and still be received inside the spring 430. Moreover, the tapered structure of the coil spring 430 narrowing toward the device side of the feedthrough 404 helps to grip the connector pin 444 in a reliable "Chinese finger trap-type"

electrical connection. Also, the silicone sleeve 426 is somewhat expandable to accommodate expansion of the coil spring 430 as the connector pin 444 is moved into the spring.

In a similar manner as the previously described header assemblies 22, 108, 200, 300 and 300A, the strain-relief device 32 comprises a proximal annular sidewall 84 joined to an intermediate annularly bevel-shaped sidewall 86. The beveled sidewall 86 extends distally as it narrows to join a cylindrically-shaped sleeve (not shown in FIGS. 23 to 27). A lumen 90 extends through the strain-relief device 32. A proximal face of the annular sidewall 84 is bonded to the body fluid side end surface 66 of the lead connector 402, for example, with an adhesive or by ultrasonic welding 450.

The strain-relief lumen 90 houses a plurality of electrical conductors (380 in FIGS. 15 to 18) of the lead 26. The proximal ends of the lead electrical conductors are connected to a respective one of the connector pins 444 of the lead connector 402. The distal ends of the lead electrical conductors are electrically connected to a lead electrode 92 (FIG. 3), as is well known by those skilled in the art. That way, with the strain-relief device 32 joined to the lead connector 402 and with the lead connector detachable connected to the feedthrough 404, there is electrical continuity from the electronic circuits or components 27 (FIG. 3A) housed inside the AMD 12 to a terminal pin 422 connected to the coil springs 430 housed inside the sleeves 426 and electrically connected to the connector pins 444 of the lead connector 402 connected to an electrical conductor of the lead 26 to a lead electrode 92. The strain-relief device 32 is also provided with spaced-apart suture openings 94 that are sized to receive a suture during a medical procedure to secure the header assembly 400 to body tissue, as is well known by those skilled in the art.

Various embodiments of header assemblies 22, 108, 200 and 400 having the feedthrough 30, 110, 210, 304, 404 of an AMD 12 connected to a lead connector 28, 112, 21, 302, 402/strain-relief device 32, 306/lead 26 assembly have been described. Those include the extending arms 44, 46 received in the lateral recess 70, 72 (FIGS. 4 and 6), the extending arms 124, 126 received in the lateral recess 154, 156 (FIGS. 8 and 9), the extending arms 224, 226 received in the lateral recess 250, 252 (FIGS. 10 and 11) and the extending arms 415, 417 received in the lateral recess 446, 448 (FIGS. 23 to 26). Other header assemblies 300 and 300A (FIGS. 17 to 23) have the extending hub 318 received to the inlet 364 of the strain-relief device 306 (FIGS. 14 to 22). In that respect, it is within the scope of the present invention that the header assemblies 300, 300A shown in FIGS. 14 to 22 are equally applicable for use with the header assemblies 22, 108, 200 and 400 shown in FIGS. 4 to 7, 8 and 9, 10 to 13 and 23 to 27, respectively. Likewise, the header assemblies 22, 108, 200 and 400 shown in FIGS. 4 to 7, 8 and 9, 10 to 13 and 23 to 27 are applicable for use with the header assemblies 300 and 300A shown in FIGS. 14 to 22.

It is appreciated that various modifications to the inventive concepts described herein may be apparent to those skilled in the art without departing from the spirit and scope of the present invention as defined by the hereinafter appended claims.

What is claimed is:

1. An active medical device (AMD) assembly, comprising:

a) an AMD comprising a device housing containing an electrical power source connected to a printed circuit board supporting at least one electronic component;

b) a feedthrough welded into an opening in the device housing, the feedthrough comprising:

i) a ferrule defining a ferrule opening extending to a ferrule device side end surface and a ferrule body fluid side end surface;

ii) an insulator hermetically sealed to the ferrule in the ferrule opening, the insulator extending to an insulator device side residing at or adjacent to the ferrule device side end surface, and the insulator extending to an insulator body fluid side residing at or adjacent to the ferrule body fluid side end surface;

iii) at least a first terminal pin and a second terminal pin supported by the insulator, wherein the first and second terminal pins each have a device side portion extending outwardly beyond the device side of the insulator and a body fluid side portion extending outwardly beyond the body fluid side of the insulator; and iv) a pair of first and second spaced-apart arms that extend distally from the body fluid side surface of the ferrule, the first and second arms having inwardly extending detents; and c) a lead connector, comprising:

i) an annular connector sidewall extending from a connector device side end surface to a connector body fluid side end surface, wherein a lateral web residing between the connector device side and body fluid side end surfaces is provided with at least a first and a second connector openings;

ii) a first proximally-facing metallic C-shaped insert and a second proximally-facing metallic C-shaped insert residing in the respective first and second connector openings;

iii) a first annular spring and a second annular spring nested in the respective first and second C-shaped inserts;

iv) a strain-relief device fixedly connected to the connector body fluid side end surface, wherein the strain-relief device is connected to a lead, the lead having at least two electrical conductors connected to respective first and second electrodes; and v) first and second lateral recesses provided in the annular connector sidewall, d) wherein, with the first and second detents of the first and second spaced-apart arms of the ferrule of the feedthrough received in the first and second lateral recesses of the lead connector:

i) the AMD is connected to the lead connector including the strain relief device, ii) the device side portions of the first and second terminal pins of the feedthrough are electrically connected to the at least one electronic component contained in the device housing, iii) the body fluid side portions of the first and second terminal pins are electrically connected to the respective first and second annular springs nested in the respective first and second C-shaped inserts, and iv) the at least two electrical conductors are electrically connected to the respective first and second C-shaped inserts and the first and second electrodes of the lead.

2. The AMD assembly of claim 1, wherein the device housing has a length extending along a longitudinal axis, and wherein first and second connector axes of the respective first and second terminal pins connected to the first and second annular springs nested in the respective first and second C-shaped inserts are aligned parallel to the longitudinal axis, and wherein, imaginary extensions of the first and second connector axes extend into the device housing.

3. The AMD assembly of claim 1, wherein the first and second C-shaped inserts each have a planar distal face, and wherein a proximal end of each of the first and second electrical conductors of the lead is angled to align with and connect to the planar distal face of the respective C-shaped insert.

4. The AMD assembly of claim 1, wherein the first and second C-shaped inserts each have a distal extension with a bore, and wherein a proximal end of each of the first and second electrical conductors is received in a respective bore to electrically connect the first and second C-shaped inserts to the first and second electrodes of the lead.

5. The AMD assembly of claim 1, wherein the ferrule has an inner annular step, and the lead connector has a protruding rim so that with the AMD medical device connected to the lead connector, the protruding rim of the lead connector is received in the annular step of the ferrule.

6. The AMD assembly of claim 5, wherein the ferrule has an inner annular groove adjacent to the annular step, the inner annular groove supporting an O-ring, and wherein, with the AMD medical device connected to the lead connector, the protruding rim of the lead connector received in the annular groove of the ferrule contacts the O-ring.

7. The AMD assembly of claim 1, wherein the lead is configured to at least one of deliver electrical stimulation to body tissue or sense biological signals from body tissue.

8. An active medical device (AMD), comprising:

a) a device housing containing an electrical power source connected to a printed circuit board supporting at least one electronic component; and b) a feedthrough welded into an opening in the device housing, the feedthrough comprising:

i) a ferrule defining a ferrule opening extending to a ferrule device side end surface and a ferrule body fluid side end surface, wherein the ferrule has an inner annular surface defining the ferrule opening, the inner annular surface having an inner annular groove;

ii) an insulator hermetically sealed to the ferrule in the ferrule opening, the insulator extending to an insulator device side residing at or adjacent to the ferrule device side end surface, and the insulator extending to an insulator body fluid side residing adjacent to the ferrule body fluid side end surface;

iii) at least a first terminal pin and a second terminal pin supported by the insulator, wherein the first and second terminal pins each have a device side portion extending outwardly beyond the device side of the insulator and a body fluid side portion extending outwardly beyond the body fluid side of the insulator;

iv) an O-ring received in the inner annular groove, wherein the O-ring resides between the insulator body fluid side and the ferrule body fluid side end surface; and v) a pair of first and second spaced-apart arms that extend distally from the body fluid side end surface of the ferrule, the first and second arms having inwardly extending first and second detents.

9. The AMD of claim 8, wherein at least one of the first and second terminal pins has a cup-shaped body fluid side portion extending outwardly beyond the body fluid side of the insulator.

10. The AMD of claim 9, wherein the ferrule has an inner annular step at the ferrule body fluid end surface, and wherein the annular step is spaced from the annular groove supporting the O-ring.

11. An active medical device (AMD), comprising:

a) a device housing containing an electrical power source connected to a printed circuit board supporting at least one electronic component; and b) a feedthrough welded into an opening in the device housing, the feedthrough comprising:

i) a ferrule defining a ferrule opening extending along a longitudinal axis to a ferrule device side end surface and a ferrule body fluid side end surface, wherein at least the ferrule device side end surface resides along an imaginary device side plane aligned perpendicular to the longitudinal axis, and wherein the ferrule has an oval shape so that in a plan view looking at the ferrule device side end surface, opposed ferrule first and second longitudinal sidewalls extend to opposed ferrule third and fourth curved end walls;

ii) an insulator hermetically sealed to the ferrule in the ferrule opening, wherein the insulator comprises opposed insulator first and second longitudinal sidewalls that extend to opposed insulator third and fourth curved end walls, and wherein the insulator sealed to the ferrule in the ferrule opening extends to an insulator device side residing at or adjacent to the ferrule device side end surface, and the insulator extending to an insulator body fluid side residing adjacent to the ferrule body fluid side end surface;

iii) at least a first terminal pin and a second terminal pin supported by the insulator, wherein the first and second terminal pins each have a device side portion extending outwardly beyond the device side of the insulator and a body fluid side portion extending outwardly beyond the body fluid side of the insulator; and iv) a pair of first and second spaced-apart arms that extend distally from the respective ferrule third and fourth curved end walls at the body fluid side end surface of the ferrule, wherein the first and second arms are spaced apart by the opposed ferrule first and second longitudinal sidewalls and comprise respective first and second arm inner walls that extend perpendicularly from the ferrule body fluid side end surface aligned along the imaginary device side plane to respective distal, inwardly extending first and second detents so that an inner apex of the first and second detents is spaced closer to the longitudinal axis than the respective perpendicularly-oriented first and second arm inner walls.

12. The AMD of claim 11, wherein the ferrule has an inner annular surface defining the ferrule opening, the inner annular surface provided with an inner annular groove, and wherein an O-ring received in the inner annular groove resides between the insulator body fluid side and the ferrule body fluid side end surface.

13. The AMD of claim 12, wherein the ferrule has an inner annular step at the ferrule body fluid end surface, and wherein the annular step is spaced from the annular groove supporting the O-ring.

* * * * *